(12) United States Patent
Mullen et al.

(10) Patent No.: US 10,032,100 B2
(45) Date of Patent: Jul. 24, 2018

(54) CARDS AND DEVICES WITH MULTIFUNCTION MAGNETIC EMULATORS AND METHODS FOR USING SAME

(71) Applicant: Dynamics Inc., Cheswick, PA (US)

(72) Inventors: Jeffrey D. Mullen, Glenshaw, PA (US); David Lambeth, Pittsburgh, PA (US); Bruce Cloutier, Jeannette, PA (US)

(73) Assignee: DYNAMICS INC., Pittsburgh, PA (US)

( * ) Notice: Subject to any disclaimer, the term of this patent is extended or adjusted under 35 U.S.C. 154(b) by 0 days.

(21) Appl. No.: 15/137,096

(22) Filed: Apr. 25, 2016

(65) Prior Publication Data

US 2016/0239735 A1    Aug. 18, 2016

Related U.S. Application Data

(63) Continuation of application No. 13/557,525, filed on Jul. 25, 2012, which is a continuation of application
(Continued)

(51) Int. Cl.
*G06K 19/00* (2006.01)
*G06K 19/06* (2006.01)
(Continued)

(52) U.S. Cl.
CPC ..... *G06K 19/06206* (2013.01); *G06F 3/0488* (2013.01); *G06K 7/0004* (2013.01);
(Continued)

(58) Field of Classification Search
USPC .......... 235/435, 439, 449, 487, 493
See application file for complete search history.

(56) References Cited

U.S. PATENT DOCUMENTS 4,353,064 A  10/1982  Stamm
4,394,654 A   7/1983  Hofmann-Cerfontaine
(Continued)

FOREIGN PATENT DOCUMENTS

EP    0203683    12/1986
GB    2420098    5/2006
(Continued)

OTHER PUBLICATIONS

U.S. Appl. No. 60/594,300, Poidomani et al.
(Continued)

*Primary Examiner* — Matthew Mikels

(57) ABSTRACT

A payment card (e.g., credit and/or debit card) is provided with a magnetic emulator operable of communicating information to a magnetic stripe reader. Information used in validating a financial transaction is encrypted based on time such that a validating server requires receipt of the appropriate encrypted information for a period of time to validate a transaction for that period of time. Such dynamic information may be communicated using such an emulator such that a card may be swiped through a magnetic stripe reader—yet communicate different information based on time. An emulator may receive information as well as communicate information to a variety of receivers (e.g., an RFID receiver).

20 Claims, 12 Drawing Sheets

Related U.S. Application Data

No. 12/339,045, filed on Dec. 19, 2008, now Pat. No. 8,517,276.

(60) Provisional application No. 61/016,491, filed on Dec. 24, 2007, provisional application No. 61/026,846, filed on Feb. 7, 2008, provisional application No. 61/027,807, filed on Feb. 11, 2008, provisional application No. 61/081,003, filed on Jul. 15, 2008, provisional application No. 61/086,239, filed on Aug. 5, 2008, provisional application No. 61/090,423, filed on Aug. 20, 2008, provisional application No. 61/097,401, filed on Sep. 16, 2008, provisional application No. 61/112,766, filed on Nov. 9, 2008, provisional application No. 61/117,186, filed on Nov. 23, 2008, provisional application No. 61/119,366, filed on Dec. 2, 2008, provisional application No. 61/120,813, filed on Dec. 8, 2008.

(51) Int. Cl.
| | |
|---|---|
| *G06K 19/07* | (2006.01) |
| *G06K 19/077* | (2006.01) |
| *G06Q 20/18* | (2012.01) |
| *G06Q 20/20* | (2012.01) |
| *G06Q 20/34* | (2012.01) |
| *G06Q 30/02* | (2012.01) |
| *G06Q 30/06* | (2012.01) |
| *G07F 7/08* | (2006.01) |
| *G07F 7/10* | (2006.01) |
| *G06K 7/08* | (2006.01) |
| *G06K 19/073* | (2006.01) |
| *G06K 7/00* | (2006.01) |
| *G06F 3/0488* | (2013.01) |

(52) U.S. Cl.
CPC ............ *G06K 7/084* (2013.01); *G06K 7/087* (2013.01); *G06K 19/06187* (2013.01); *G06K 19/07* (2013.01); *G06K 19/0704* (2013.01); *G06K 19/0723* (2013.01); *G06K 19/0725* (2013.01); *G06K 19/0775* (2013.01); *G06K 19/07345* (2013.01); *G06K 19/07703* (2013.01); *G06K 19/07705* (2013.01); *G06K 19/07707* (2013.01); *G06K 19/07709* (2013.01); *G06K 19/07749* (2013.01); *G06K 19/07766* (2013.01); *G06K 19/07769* (2013.01); *G06K 19/07773* (2013.01); *G06Q 20/18* (2013.01); *G06Q 20/20* (2013.01); *G06Q 20/34* (2013.01); *G06Q 20/341* (2013.01); *G06Q 20/3415* (2013.01); *G06Q 20/352* (2013.01); *G06Q 30/0222* (2013.01); *G06Q 30/0241* (2013.01); *G06Q 30/0277* (2013.01); *G06Q 30/0641* (2013.01); *G07F 7/0806* (2013.01); *G07F 7/1008* (2013.01)

(56) References Cited

U.S. PATENT DOCUMENTS

| | | |
|---|---|---|
| 4,614,861 A | 9/1986 | Pavlov et al. |
| 4,667,087 A | 5/1987 | Quintana |
| 4,701,601 A | 10/1987 | Francini et al. |
| 4,720,860 A | 1/1988 | Weiss |
| 4,786,791 A | 11/1988 | Hodama |
| 4,789,776 A | 12/1988 | Inoue |
| 4,791,283 A | 12/1988 | Burkhardt |
| 4,797,542 A | 1/1989 | Hara |
| 4,902,146 A | 2/1990 | Ishikawa |
| 5,038,251 A | 8/1991 | Sugiyama et al. |
| 5,166,774 A | 11/1992 | Banerji et al. |
| 5,168,520 A | 12/1992 | Weiss |
| 5,237,614 A | 8/1993 | Weiss |
| 5,254,843 A | 10/1993 | Hynes et al. |
| 5,276,311 A | 1/1994 | Hennige |
| 5,347,580 A | 9/1994 | Molva et al. |
| 5,361,062 A | 11/1994 | Weiss et al. |
| 5,412,199 A | 5/1995 | Finkelstein et al. |
| 5,434,398 A | 7/1995 | Goldberg |
| 5,434,405 A | 7/1995 | Finkelstein et al. |
| 5,477,038 A | 12/1995 | Levine et al. |
| 5,478,994 A | 12/1995 | Rahman |
| 5,479,512 A | 12/1995 | Weiss |
| 5,484,997 A | 1/1996 | Haynes |
| 5,485,519 A | 1/1996 | Weiss |
| 5,521,831 A | 5/1996 | May |
| 5,585,787 A | 12/1996 | Wallerstein |
| 5,591,949 A | 1/1997 | Bernstein |
| 5,608,203 A | 3/1997 | Finkelstein et al. |
| 5,623,552 A | 4/1997 | Lane |
| 5,657,388 A | 8/1997 | Weiss |
| 5,748,737 A | 5/1998 | Daggar |
| 5,834,747 A | 11/1998 | Cooper |
| 5,834,756 A | 11/1998 | Gutman et al. |
| 5,838,549 A | 11/1998 | Nagata et al. |
| 5,856,661 A | 1/1999 | Finkelstein et al. |
| 5,864,623 A | 1/1999 | Messina et al. |
| 5,886,874 A | 3/1999 | Onoda et al. |
| 5,907,142 A | 5/1999 | Kelsey |
| 5,913,203 A | 6/1999 | Wong et al. |
| 5,937,394 A | 8/1999 | Wong et al. |
| 5,941,375 A | 8/1999 | Kamens et al. |
| 5,955,021 A | 9/1999 | Tiffany, III |
| 5,955,961 A | 9/1999 | Wallerstein |
| 5,956,699 A | 9/1999 | Wong et al. |
| 6,012,636 A | 1/2000 | Smith |
| 6,025,054 A | 2/2000 | Tiffany, III |
| 6,045,043 A | 4/2000 | Bashan et al. |
| 6,076,163 A | 6/2000 | Hoffstein et al. |
| 6,085,320 A | 7/2000 | Kaliski |
| 6,095,416 A | 8/2000 | Grant et al. |
| 6,129,277 A | 10/2000 | Grant et al. |
| 6,130,621 A | 10/2000 | Weiss |
| 6,145,079 A | 11/2000 | Mitty et al. |
| 6,157,920 A | 12/2000 | Jakobsson et al. |
| 6,161,181 A | 12/2000 | Haynes, III et al. |
| 6,176,430 B1 | 1/2001 | Finkelstein et al. |
| 6,182,894 B1 | 2/2001 | Hackett et al. |
| 6,189,098 B1 | 2/2001 | Kaliski |
| 6,199,052 B1 | 3/2001 | Mitty et al. |
| 6,206,293 B1 | 3/2001 | Gutman et al. |
| 6,240,184 B1 | 5/2001 | Huynh et al. |
| 6,241,153 B1 | 6/2001 | Tiffany, III |
| 6,256,873 B1 | 7/2001 | Tiffany, III |
| 6,269,163 B1 | 7/2001 | Rivest et al. |
| 6,286,022 B1 | 9/2001 | Kaliski et al. |
| 6,308,890 B1 | 10/2001 | Cooper |
| 6,313,724 B1 | 11/2001 | Osterweil |
| 6,389,442 B1 | 5/2002 | Yin et al. |
| 6,393,447 B1 | 5/2002 | Jakobsson et al. |
| 6,402,029 B1 | 6/2002 | Gangi |
| 6,411,715 B1 | 6/2002 | Liskov et al. |
| 6,446,052 B1 | 9/2002 | Juels |
| 6,460,141 B1 | 10/2002 | Olden |
| 6,592,044 B1 | 7/2003 | Wong et al. |
| 6,607,127 B2 | 8/2003 | Wong |
| 6,609,654 B1 | 8/2003 | Anderson et al. |
| 6,631,849 B2 | 10/2003 | Blossom |
| 6,655,585 B2 | 12/2003 | Shinn |
| 6,681,988 B2 | 1/2004 | Stack et al. |
| 6,705,520 B1 | 3/2004 | Pitroda et al. |
| 6,755,341 B1 | 6/2004 | Wong et al. |
| 6,764,005 B2 | 7/2004 | Cooper |
| 6,769,618 B1 | 8/2004 | Finkelstein |
| 6,805,288 B2 | 10/2004 | Routhenstein et al. |
| 6,811,082 B2 | 11/2004 | Wong |
| 6,813,354 B1 | 11/2004 | Jakobsson et al. |
| 6,817,532 B2 | 11/2004 | Finkelstein |
| 6,873,974 B1 | 3/2005 | Schutzer |
| 6,883,714 B2 | 4/2005 | Keogh |

(56) References Cited

U.S. PATENT DOCUMENTS

| | | |
|---|---|---|
| 6,902,116 B2 | 6/2005 | Finkelstein |
| 6,970,070 B2 | 11/2005 | Juels et al. |
| 6,980,969 B1 | 12/2005 | Tuchler et al. |
| 6,985,583 B1 | 1/2006 | Brainard et al. |
| 6,991,155 B2 | 1/2006 | Burchette, Jr. |
| 7,013,030 B2 | 3/2006 | Wong et al. |
| 7,035,443 B2 | 4/2006 | Wong |
| 7,039,223 B2 | 5/2006 | Wong |
| 7,044,394 B2 | 5/2006 | Brown |
| 7,051,929 B2 | 5/2006 | Li |
| 7,083,094 B2 | 8/2006 | Cooper |
| 7,100,049 B2 | 8/2006 | Gasparini et al. |
| 7,100,821 B2 | 9/2006 | Rasti |
| 7,111,172 B1 | 9/2006 | Duane et al. |
| 7,114,652 B2 | 10/2006 | Moullette et al. |
| 7,136,514 B1 | 11/2006 | Wong |
| 7,140,550 B2 | 11/2006 | Ramachandran |
| 7,163,153 B2 | 1/2007 | Blossom |
| 7,195,154 B2 | 3/2007 | Routhenstein |
| 7,195,160 B2 | 3/2007 | Ison et al. |
| 7,197,639 B1 | 3/2007 | Juels et al. |
| 7,219,368 B2 | 5/2007 | Juels et al. |
| 7,225,537 B2 | 6/2007 | Reed |
| 7,225,994 B2 | 6/2007 | Finkelstein |
| 7,246,752 B2 | 7/2007 | Brown |
| 7,298,243 B2 | 11/2007 | Juels et al. |
| 7,334,732 B2 | 2/2008 | Cooper |
| 7,337,326 B2 | 2/2008 | Palmer et al. |
| 7,346,775 B2 | 3/2008 | Gasparini et al. |
| 7,356,696 B1 | 4/2008 | Jakobsson et al. |
| 7,357,319 B1 | 4/2008 | Lin et al. |
| 7,359,507 B2 | 4/2008 | Kaliski |
| 7,360,688 B1 | 4/2008 | Harris |
| 7,363,494 B2 | 4/2008 | Brainard et al. |
| 7,364,092 B2 | 4/2008 | Narendra et al. |
| 7,370,805 B2 | 5/2008 | Smith et al. |
| 7,380,710 B2 | 6/2008 | Brown |
| 7,398,253 B1 | 7/2008 | Pinnell |
| 7,404,087 B2 | 7/2008 | Teunen |
| 7,424,570 B2 | 9/2008 | D'Albore et al. |
| 7,427,033 B1 | 9/2008 | Roskind |
| 7,441,709 B2 | 10/2008 | Chan et al. |
| 7,454,349 B2 | 11/2008 | Teunen et al. |
| 7,461,250 B1 | 12/2008 | Duane et al. |
| 7,461,399 B2 | 12/2008 | Juels et al. |
| 7,472,093 B2 | 12/2008 | Juels |
| 7,472,829 B2 | 1/2009 | Brown |
| 7,494,055 B2 | 2/2009 | Fernandes et al. |
| 7,502,467 B2 | 3/2009 | Brainard et al. |
| 7,502,933 B2 | 3/2009 | Jakobsson et al. |
| 7,503,485 B1 | 3/2009 | Routhenstein |
| 7,516,492 B1 | 4/2009 | Nisbet et al. |
| 7,523,301 B2 | 4/2009 | Nisbet et al. |
| 7,530,495 B2 | 5/2009 | Cooper |
| 7,532,104 B2 | 5/2009 | Juels |
| 7,543,739 B2 | 6/2009 | Brown et al. |
| 7,559,464 B2 | 7/2009 | Routhenstein |
| 7,562,221 B2 | 7/2009 | Nystrom et al. |
| 7,562,222 B2 | 7/2009 | Gasparini et al. |
| 7,580,898 B2 | 8/2009 | Brown et al. |
| 7,584,153 B2 | 9/2009 | Brown et al. |
| 7,591,416 B2 | 9/2009 | Blossom |
| 7,591,426 B2 | 9/2009 | Osterweil et al. |
| 7,591,427 B2 | 9/2009 | Osterweil |
| 7,602,904 B2 | 10/2009 | Juels et al. |
| 7,631,804 B2 | 12/2009 | Brown |
| 7,639,537 B2 | 12/2009 | Sepe et al. |
| 7,641,124 B2 | 1/2010 | Brown et al. |
| 7,660,902 B2 | 2/2010 | Graham et al. |
| 7,828,207 B2 | 11/2010 | Cooper |
| 7,996,318 B2 | 8/2011 | Marcon |
| 2001/0034702 A1 | 10/2001 | Mockett et al. |
| 2001/0047335 A1 | 11/2001 | Arndt et al. |
| 2002/0032657 A1 | 3/2002 | Singh |
| 2002/0043566 A1 | 4/2002 | Goodman et al. |
| 2002/0059114 A1 | 5/2002 | Cockrill et al. |
| 2002/0070976 A1 | 6/2002 | Tanner et al. |
| 2002/0082989 A1 | 6/2002 | Fife et al. |
| 2002/0096570 A1 | 7/2002 | Wong et al. |
| 2002/0120583 A1 | 8/2002 | Keresman, III et al. |
| 2002/0153424 A1 | 10/2002 | Chuan |
| 2003/0034388 A1 | 2/2003 | Routhenstein et al. |
| 2003/0052168 A1 | 3/2003 | Wong |
| 2003/0057278 A1 | 3/2003 | Wong |
| 2003/0069846 A1 | 4/2003 | Marcon |
| 2003/0085286 A1* | 5/2003 | Kelley ............ G06K 19/073 235/492 |
| 2003/0098780 A1 | 5/2003 | Taylor et al. |
| 2003/0116635 A1 | 6/2003 | Taban |
| 2003/0152253 A1 | 8/2003 | Wong |
| 2003/0163287 A1 | 8/2003 | Vock et al. |
| 2003/0173409 A1 | 9/2003 | Vogt et al. |
| 2003/0179909 A1 | 9/2003 | Wong et al. |
| 2003/0179910 A1 | 9/2003 | Wong |
| 2003/0209608 A1 | 11/2003 | Blossom |
| 2003/0218066 A1 | 11/2003 | Fernandes et al. |
| 2003/0226899 A1 | 12/2003 | Finkelstein |
| 2004/0011877 A1 | 1/2004 | Reppermund |
| 2004/0035942 A1 | 2/2004 | Silverman |
| 2004/0055770 A1 | 3/2004 | Babb |
| 2004/0133787 A1 | 7/2004 | Doughty |
| 2004/0159700 A1 | 8/2004 | Khan et al. |
| 2004/0162732 A1 | 8/2004 | Rahim et al. |
| 2004/0172535 A1 | 9/2004 | Jakobsson |
| 2004/0177045 A1 | 9/2004 | Brown |
| 2005/0001711 A1 | 1/2005 | Doughty et al. |
| 2005/0043997 A1 | 2/2005 | Sahota et al. |
| 2005/0080747 A1 | 4/2005 | Anderson et al. |
| 2005/0086160 A1 | 4/2005 | Wong et al. |
| 2005/0086177 A1 | 4/2005 | Anderson et al. |
| 2005/0092830 A1 | 5/2005 | Blossom |
| 2005/0116026 A1 | 6/2005 | Burger et al. |
| 2005/0119940 A1 | 6/2005 | Concilio et al. |
| 2005/0133590 A1 | 6/2005 | Rettenmyer et al. |
| 2005/0154643 A1 | 7/2005 | Doan et al. |
| 2005/0194452 A1 | 9/2005 | Nordentoft et al. |
| 2005/0219728 A1 | 10/2005 | Durbin et al. |
| 2005/0228959 A1 | 10/2005 | D'Albore et al. |
| 2005/0230788 A1 | 10/2005 | Kato et al. |
| 2005/0274803 A1 | 12/2005 | Lee |
| 2006/0000900 A1 | 1/2006 | Fernandes et al. |
| 2006/0017570 A1 | 1/2006 | Moskowitz et al. |
| 2006/0037073 A1 | 2/2006 | Juels et al. |
| 2006/0041759 A1 | 2/2006 | Kaliski et al. |
| 2006/0054699 A1 | 3/2006 | Osterweil |
| 2006/0085043 A1 | 4/2006 | Stevenson |
| 2006/0085328 A1 | 4/2006 | Cohen et al. |
| 2006/0091223 A1 | 5/2006 | Zellner |
| 2006/0124748 A1 | 6/2006 | Osborn et al. |
| 2006/0161435 A1 | 7/2006 | Atef et al. |
| 2006/0161789 A1 | 7/2006 | Doughty et al. |
| 2006/0163353 A1 | 7/2006 | Moulette et al. |
| 2006/0174104 A1 | 8/2006 | Crichton et al. |
| 2006/0186209 A1 | 8/2006 | Narendra et al. |
| 2006/0196931 A1 | 9/2006 | Holtmanns et al. |
| 2006/0217792 A1 | 9/2006 | Hussein et al. |
| 2006/0227523 A1 | 10/2006 | Pennaz et al. |
| 2006/0241236 A1 | 10/2006 | Kuznetsov et al. |
| 2006/0249574 A1 | 11/2006 | Brown et al. |
| 2006/0256961 A1 | 11/2006 | Brainard et al. |
| 2006/0262655 A1 | 11/2006 | Persson |
| 2006/0283958 A1 | 12/2006 | Osterweil |
| 2007/0023532 A1 | 2/2007 | Narendra et al. |
| 2007/0029110 A1 | 2/2007 | Matsumoto et al. |
| 2007/0034700 A1* | 2/2007 | Poidomani ........ G06K 19/0702 235/492 |
| 2007/0040030 A1 | 2/2007 | Kranzley et al. |
| 2007/0063804 A1 | 3/2007 | Watanabe |
| 2007/0114274 A1 | 5/2007 | Gibbs et al. |
| 2007/0124321 A1 | 5/2007 | Szydlo |
| 2007/0131759 A1 | 6/2007 | Cox et al. |
| 2007/0136211 A1 | 6/2007 | Brown et al. |
| 2007/0152052 A1 | 7/2007 | Sines |
| 2007/0152070 A1 | 7/2007 | D'Albore |

(56) References Cited

U.S. PATENT DOCUMENTS

| | | |
|---|---|---|
| 2007/0152072 A1 | 7/2007 | Frallicciardi et al. |
| 2007/0153487 A1 | 7/2007 | Frallicciardi et al. |
| 2007/0158439 A1 | 7/2007 | Conner et al. |
| 2007/0174614 A1 | 7/2007 | Duane et al. |
| 2007/0189591 A1 | 8/2007 | Lu et al. |
| 2007/0241183 A1 | 10/2007 | Brown et al. |
| 2007/0241201 A1 | 10/2007 | Brown et al. |
| 2007/0256123 A1 | 11/2007 | Duane et al. |
| 2007/0267503 A1 | 11/2007 | Dewan |
| 2007/0192249 A1 | 12/2007 | Biffle et al. |
| 2007/0291753 A1 | 12/2007 | Romano |
| 2008/0005510 A1 | 1/2008 | Sepe et al. |
| 2008/0008315 A1 | 1/2008 | Fontana et al. |
| 2008/0008322 A1 | 1/2008 | Fontana et al. |
| 2008/0010675 A1 | 1/2008 | Massascusa et al. |
| 2008/0016351 A1 | 1/2008 | Fontana et al. |
| 2008/0019507 A1 | 1/2008 | Fontana et al. |
| 2008/0028447 A1 | 1/2008 | O'Malley et al. |
| 2008/0040271 A1 | 2/2008 | Hammad et al. |
| 2008/0040276 A1 | 2/2008 | Hammad et al. |
| 2008/0058016 A1 | 3/2008 | Di Maggio et al. |
| 2008/0059379 A1 | 3/2008 | Ramaci et al. |
| 2008/0093467 A1 | 4/2008 | Narendra et al. |
| 2008/0096326 A1 | 4/2008 | Reed |
| 2008/0116283 A1* | 5/2008 | Newbrough ............ B67B 7/16 235/487 |
| 2008/0116285 A1 | 5/2008 | Shoemaker |
| 2008/0121726 A1 | 5/2008 | Brady et al. |
| 2008/0126262 A1 | 5/2008 | Brady et al. |
| 2008/0126398 A1 | 5/2008 | Cimino |
| 2008/0128515 A1 | 6/2008 | Di Iorio |
| 2008/0148393 A1 | 6/2008 | Wendt |
| 2008/0148394 A1 | 6/2008 | Poidomani et al. |
| 2008/0150123 A1 | 6/2008 | Li et al. |
| 2008/0201264 A1 | 8/2008 | Brown et al. |
| 2008/0209550 A1 | 8/2008 | Di Iorio |
| 2008/0217396 A1 | 9/2008 | Boalt |
| 2008/0223937 A1 | 9/2008 | Preta et al. |
| 2008/0245851 A1* | 10/2008 | Kowalski ............ G06K 7/10178 235/375 |
| 2008/0262825 A1 | 10/2008 | Haid et al. |
| 2008/0288699 A1 | 11/2008 | Chichierchia |
| 2008/0290166 A1 | 11/2008 | von Mueller |
| 2008/0294930 A1 | 11/2008 | Varone et al. |
| 2008/0302877 A1 | 12/2008 | Musella et al. |
| 2009/0006262 A1 | 1/2009 | Brown et al. |
| 2009/0013122 A1 | 1/2009 | Sepe et al. |
| 2009/0036147 A1 | 2/2009 | Romano |
| 2009/0046522 A1 | 2/2009 | Sepe et al. |
| 2009/0048971 A1 | 2/2009 | Hathaway et al. |
| 2009/0055893 A1 | 2/2009 | Manessis et al. |
| 2009/0078761 A1 | 3/2009 | Sines |
| 2009/0108064 A1 | 4/2009 | Fernandes et al. |
| 2009/0134218 A1 | 5/2009 | Yuzon et al. |
| 2009/0150295 A1 | 6/2009 | Hatch et al. |
| 2009/0152365 A1 | 6/2009 | Li et al. |
| 2009/0164380 A1 | 6/2009 | Brown |
| 2009/0166435 A1 | 7/2009 | Blythe |
| 2009/0200367 A1 | 8/2009 | Arnouse |
| 2009/0206165 A1 | 8/2009 | Laackmann et al. |
| 2009/0242648 A1 | 10/2009 | Di Sirio et al. |
| 2009/0244858 A1 | 10/2009 | Di Sirio et al. |
| 2009/0253460 A1 | 10/2009 | Varone et al. |
| 2009/0255996 A1 | 10/2009 | Brown et al. |
| 2009/0261161 A1 | 11/2009 | Blossom |
| 2009/0290704 A1 | 11/2009 | Cimino |
| 2009/0303885 A1 | 12/2009 | Longo |
| 2010/0127830 A1 | 5/2010 | Nielsen et al. |
| 2010/0224684 A1 | 9/2010 | Bonnin et al. |
| 2010/0265617 A1 | 10/2010 | Isuyama |
| 2010/0270373 A1 | 10/2010 | Poidomani et al. |
| 2011/0028184 A1 | 2/2011 | Cooper |
| 2011/0050164 A1 | 3/2011 | Partovi et al. |
| 2011/0084149 A1 | 4/2011 | Faith et al. |
| 2011/0117838 A1 | 5/2011 | Bosquet et al. |
| 2011/0140538 A1 | 6/2011 | Jung et al. |
| 2011/0272465 A1 | 11/2011 | Mullen et al. |
| 2011/0272475 A1 | 11/2011 | Mullen et al. |

FOREIGN PATENT DOCUMENTS

| | | |
|---|---|---|
| JP | 05210770 A | 8/1993 |
| JP | 11087989 | 3/1999 |
| JP | 2004165400 | 12/2005 |
| WO | WO9852735 | 11/1998 |
| WO | WO0247019 | 6/2002 |
| WO | WO06066322 | 6/2006 |
| WO | WO06080929 | 8/2006 |
| WO | WO06105092 | 10/2006 |
| WO | WO06116772 | 11/2006 |
| WO | WO07141779 | 12/2007 |
| WO | WO08064403 | 6/2008 |

OTHER PUBLICATIONS

U.S. Appl. No. 60/675,388, Poidomani et al.
The Bank Credit Card Business. Second Edition, American Bankers Association, Washington, D.C., 1996.
A Day in the Life of a Flux Reversal. http://www.phrack/org/issues. html?issue=37&id=6#article. As viewed on Apr. 12, 2010.
Dynamic Virtual Credit Card Numbers. http://homes.cerias.purdue. edu/~jtli/paper/fc07.pdf. As viewed on Apr. 12, 2010.
USPTO, International Search Report, dated Apr. 28, 2009.
English translation of JP 05210770 A.
EPO, Extended European Search Report, dated Jan. 26, 2012.

* cited by examiner

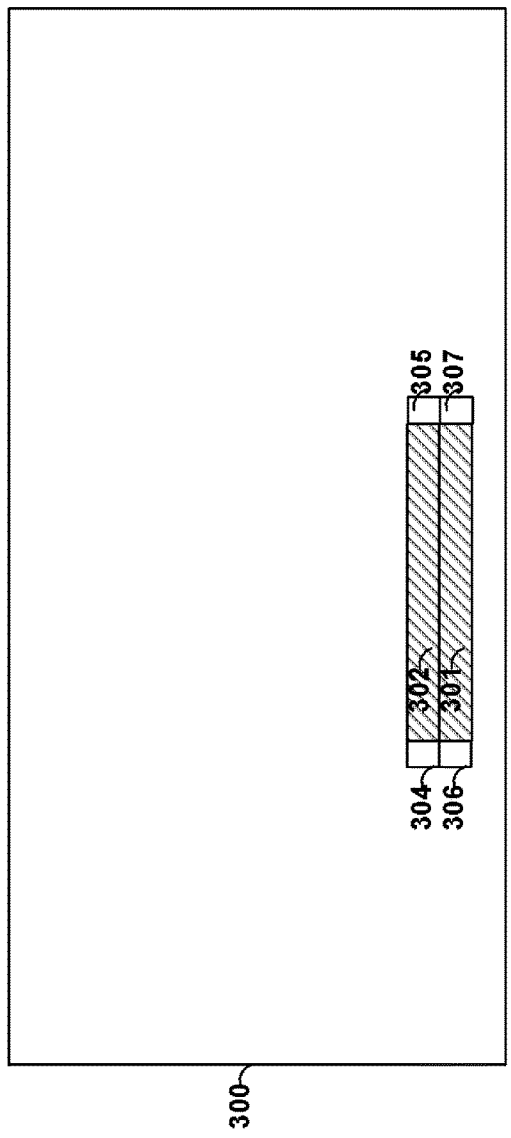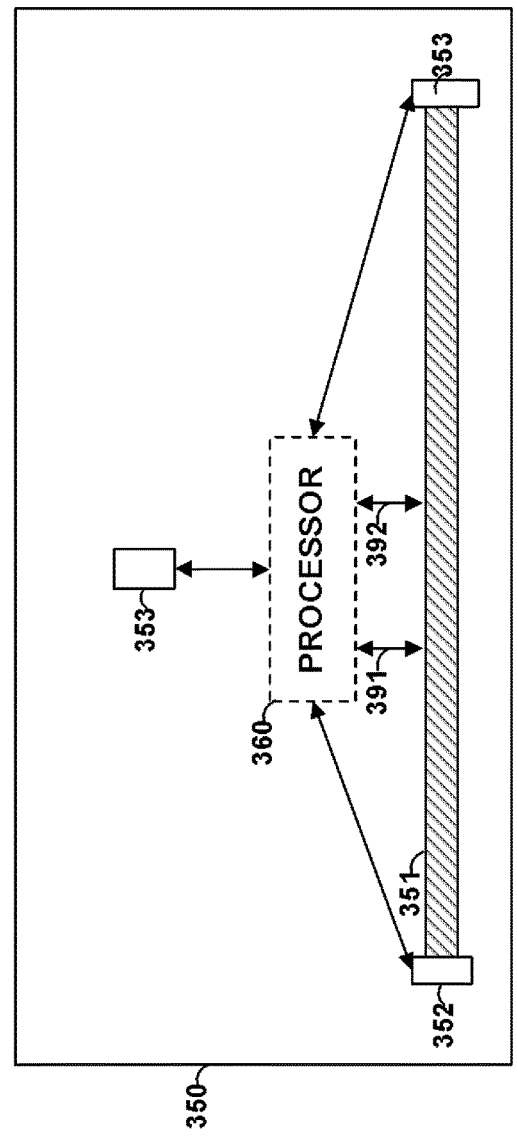
FIG. 3

CARDS AND DEVICES WITH MULTIFUNCTION MAGNETIC EMULATORS AND METHODS FOR USING SAME

CROSS-REFERENCE TO RELATED APPLICATIONS

This application is a continuation of U.S. patent application Ser. No. 13/557,525, filed on Jul. 25, 2012, which claims the benefit of U.S. Pat. No. 8,517,276, filed on Dec. 19, 2008, which claims the benefit of U.S. Provisional Patent Application Nos. 61/016,491 filed on Dec. 24, 2007, 61/026, 846 filed on Feb. 7, 2008, 61/027,807 filed on Feb. 11, 2008, 61/081,003 filed on Jul. 15, 2008, 61/086,239 filed on Aug. 5, 2008, 61/090,423 filed on Aug. 20, 2008, 61/097,401 filed Sep. 16, 2008, 61/112,766 filed on Nov. 9, 2008, 61/117,186 filed on Nov. 23, 2008, 61/119,366 filed on Dec. 2, 2008, and 61/120,813 filed on Dec. 8, 2008, all of which are hereby incorporated by reference herein in their entirety.

BACKGROUND OF THE INVENTION

This invention relates to magnetic cards and payment systems.

SUMMARY OF THE INVENTION

A card is provided, such as a credit card or security card, that may transmit information to a magnetic stripe reader via a magnetic emulator. The magnetic emulator may be, for example, a circuit that emits electromagnetic fields operable to electrically couple with a read-head of a magnetic stripe reader such that data may be transmitted from the circuit to the magnetic stripe reader. The emulator may be operated serially such that information is transmitted serially to a magnetic stripe reader. Alternatively, for example, portions of a magnetic emulator may emit different electromagnetic fields at a particular instance such that the emulator is operated to provide physically parallel, instantaneous data. Alternatively still, a magnetic medium may be provided and a circuit may be provided to change the magnetic properties of the magnetic medium such that a magnetic stripe reader is operable to read information written on the magnetic medium.

A processor may be provided on a card, or other device, that controls a magnetic emulator. The processor may be configured to operate the emulator such that the emulator transmits serial or parallel information. Particularly, the processor may decouple portions of an emulator from one another such that different portions of the emulator may transmit different information (e.g., transmit data in a parallel operation). The processor may couple portions of an emulator together (or drive the portions together) such that all portions of the emulator transmits the same information (e.g., transmit data in a serial operation). Alternatively, the processor may drive a portion of the emulator to transmit data using one method (e.g., serially) while the processor drives another portion of the emulator using a different method (e.g., in parallel).

The processor may drive an emulator through a switching circuit. The switching circuit may control the direction and magnitude of current that flows through at least a portion of an emulator such that the switching circuit controls the direction and magnitude of the electromagnetic field created by at least that portion of the emulator. An electromagnetic field may be generated by the emulator such that the emulator is operable to electrically couple with a read-head from a magnetic stripe reader without making physical contact with the read-head. Particularly, for example, an emulator that is driven with increased current can be operable to couple with the read-head of a magnetic stripe reader even when placed outside and within the proximity of (e.g., 0.25 inches) the read-head.

A magnetic emulator may be operated to electrically couple, and transmit data to, devices other than a magnetic stripe reader. For example, a magnetic emulator may be operated to electrically couple, and transmit data to, a device using a Radio Frequency IDentification (RFID) protocol. Accordingly, a processor may drive the emulator at a frequency and magnitude in order to electrically couple with a read-head of a magnetic stripe reader and then drive the emulator at a different frequency and a different magnitude in order to electronically couple with an RFID reader.

A processor may receive information from a magnetic stripe reader detector and/or an RFID receiver detector. A processor may detect, for example, the presence of a read-head of a magnetic stripe reader by receiving signals from a magnetic stripe reader detector and, in response, the processor may drive a magnetic emulator in a manner that allows the emulator to couple with the magnetic stripe reader. The processor may also detect, for example, the presence of and RFID receiver by receiving signals from an RFID receiver detector and, in response, the processor may drive a magnetic emulator in a manner that allows the emulator to couple with the RFID receiver. More than one emulator may be provided on a card or other device and a processor may drive such emulators in a variety of different manners.

A circuit may be provided on a credit card that is operable to receive data from a magnetic stripe encoder and/or an RFID transmitter. Such a circuit may electrically couple with an RFID transmitter and/or magnetic stripe encoder and deliver information to a processor. In this manner, a card, or other device, may communicate bi-directionally with a device.

An emulator may communicate with a magnetic stripe reader outside of, for example, the housing of a magnetic stripe reader. Accordingly, for example, the emulator may be provided in devices other than cards sized to fit inside of the reading area of a magnetic stripe reader. In other words, for example, the emulator may be located in a device that is thicker than a card—yet the emulator can still communicate with one or more read-heads located in a magnetic stripe reader. Such a device may be, for example, a security token, a wireless communications device, a laptop, a Personal Digital Assistant (PDA), a physical lock key to a house and/or car, or any other device.

Dynamic information may be provided by a processor located on the card, or other device, and communicated through a magnetic emulator. Such dynamic information may, for example, change based on time. For example, the dynamic information may be periodically encrypted differently. One or more displays may be located on a card, or other device, such that the dynamic information may be displayed to a user through the display. Buttons may be provided to accept input from a user to, for example, control the operation of the card or other device.

Dynamic information may include, for example, a dynamic number that is used as, or part of, a number for a credit card number, debit card number, payment card number, and/or payment verification code. Dynamic information may also include, for example, a student identification number or medical identification number. Dynamic information may also, for example, include alphanumeric information such that a dynamic account name is provided.

BRIEF DESCRIPTION OF THE DRAWINGS

The principles and advantages of the present invention can be more clearly understood from the following detailed description considered in conjunction with the following drawings, in which the same reference numerals denote the same structural elements throughout, and in which:

FIG. 3 is an illustration of cards constructed in accordance with the principles of the present invention;

DETAILED DESCRIPTION OF THE INVENTION

Figure 1:
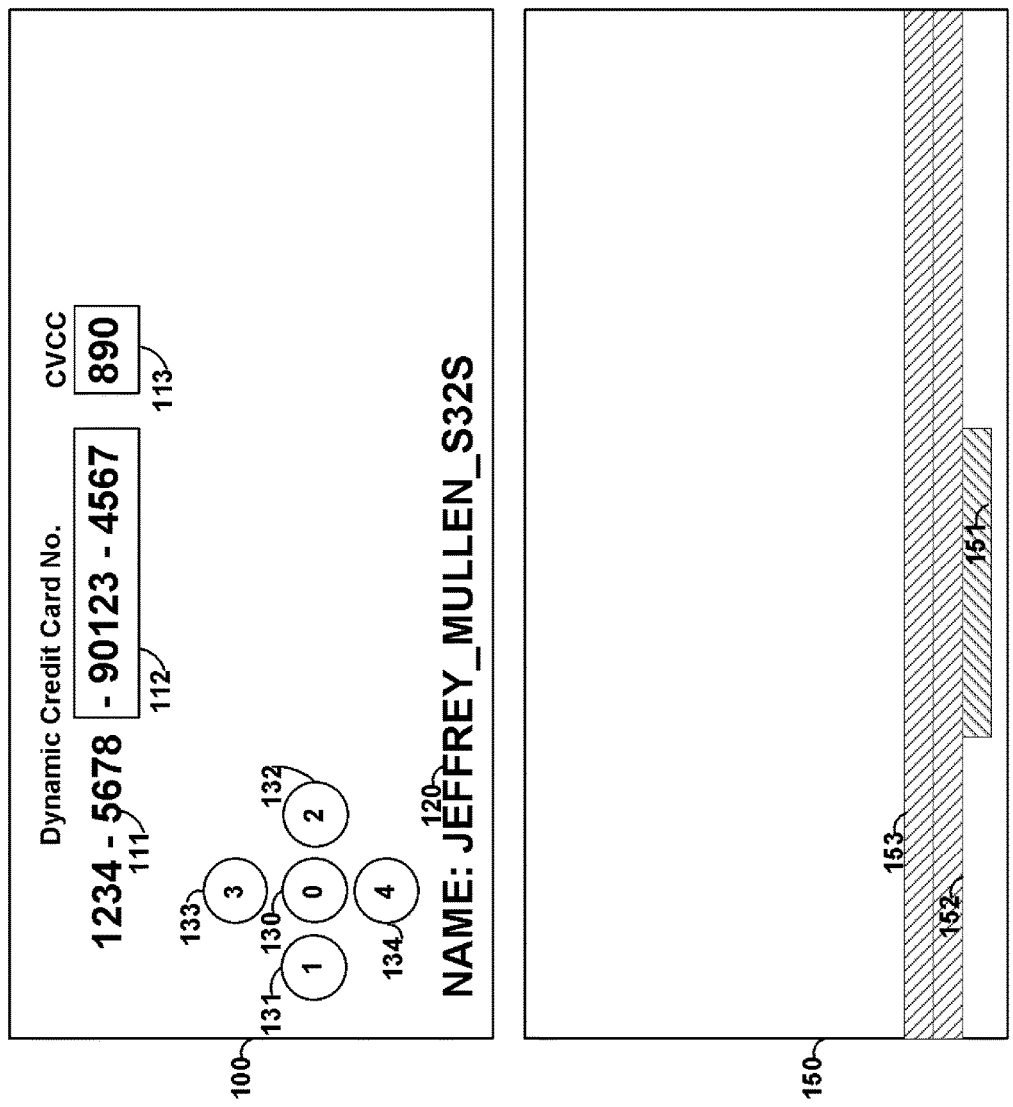
FIG. 1 is an illustration of cards constructed in accordance with the principles of the present invention.

FIG. 1 shows card 100 that includes printed information 111 and 120, displays 112 and 113, and buttons 130-134. Card 100 may be, for example, a payment card such as a credit card, debit card, and/or gift card. Payment information, such as a credit/debit card number may be provided as static information 111, dynamic information 112 and/or 113, or any combination thereof.

For example, a particular number of digits of a credit card number (e.g., the last 3 digits) may be provided as dynamic information. Such dynamic information may be changed periodically (e.g., once every hour). Information may be changed via, for example, encryption. Software may be provided at, for example, the payment verification servers that verifies the dynamic information for each period of time such that a payment can be validated and processed for a particular user. A user may be identifies using, for example, static information that is used to form a credit card number or other static information (e.g., information 120). Additionally, identification information may be derived (e.g., embedded) in dynamic information. Persons skilled in the art will appreciate that a credit card number may have, for example, a length of 15 or 16 digits. A credit card number may also have a length of up to 19 digits. A verification code may be used with some payment systems and such a verification code may be provided statically on the card or may be provided as dynamic information. Such a verification code may be provided on a second display located on, for example, the front or rear surface of card 100. Alternatively, a verification code may be displayed on the same display as other dynamic information (e.g., dynamic information 112). A display may be, for example, a flexible electronic ink display. Such a flexible electronic ink display may, for example, utilize power to change displayed information, but may not utilize power to display information after the information is changed.

Card 150 may be provided. Card 150 may include static magnetic stripe tracks 153 and 152. A magnetic emulator may be provided as device 151. Device 151 may be operable to electrically couple with a read-head of a magnetic stripe reader. Persons skilled in the art will appreciate that a read-head housing of a magnetic stripe reader may be provided with one, two, or three active read-heads that are operable to each couple with a separate magnetic track of information. A reader may also have more than one read-head housing and each read-head housing may be provided with one, two, or three active read-heads that are operable to each couple with a separate magnetic track of information. Such read-head housings may be provided different surfaces of a magnetic stripe reader. For example, the read-head housings may be provided on opposite walls of a trough sized to accept payment cards. Accordingly, the devices on the opposite sides of the trough may be able to read a credit card regardless of the direction that the credit card was swiped.

A magnetic emulator may be provided and may be positioned on card 150 such that when card 150 is swiped through a credit card reader, the magnetic emulator passes underneath, or in the proximity of, a read-head for a particular magnetic track. An emulator may be large enough to simultaneously pass beneath, or in the proximity of, multiple read-heads. Information may be transmitted, for example, serially to one or more read-heads. Information from different tracks of data may also be transmitted serially and the magnetic stripe reader may determine the different data received by utilize the starting and/or ending sentinels that define the information for each track. A magnetic emulator may also transmit a string of leading and/or ending zeros such that a magnetic reader may utilize such a string of zeros to provide self-clocking. In doing so, for example, information may be transmitted serially at high speeds to a magnetic stripe reader. For example, credit card information may be transmitted to a magnetic stripe reader at speeds up to, and greater than, 30 Khz).

Different emulators may be provided, and positioned, on card 150 to each couple with a different read-head and each emulator may provide different track information to those different read-heads. Read-head detectors may be utilized to detect when a read-head is over an emulator such that an emulator is controlled by a processor to operate when a read-head detector detects the appropriate presence of a read-head. In doing so, power may be saved. Additionally, the read-head detector may detect how many read-heads are reading the card and, accordingly, only communicate with the associated emulators. In doing so, additional power may be conserved. Accordingly, an emulator may be utilized to communicate dynamic information to a magnetic stripe reader. Such dynamic information may include, for example, dynamic payment card information that changes based on time.

A static magnetic stripe may be provide to transmit data for one or more tracks to a magnetic strip reader where dynamic information is not desired. Card 150, for example, may include static magnetic track 153 and static magnetic track 152. Information on static magnetic tracks 152 and 153 may be encoded via a magnetic stripe encoder. Device 151 may include an emulator such that dynamic information may be communicated through emulator 151. Any combination of emulators and static magnetic tracks may be utilized for a card or device.

One or more batteries, such as flexible lithium polymer, batteries may be utilized to form card 100. Such batteries may be electrically coupled in a serial combination to provide a source of power to the various components of card 100. Alternatively, separate batteries may provide power to different components of card 100. For example, a battery may provide power to a processor and/or display of card 100, while another battery provides a source of energy to one or more magnetic emulators of card 100. In doing so, for example, a processor may operate even after the battery that supplies power to an emulator completely discharges. Accordingly, the processor may provide information to another component of card 100. For example, the processor may display information on a display to indicate to a user that the magnetic emulator is not longer operational due to power exhaustion. Batteries may be, for example, rechargeable and contacts, or other devices, may be provided on card 100 such that the battery may be recharged.

Buttons (e.g., buttons 130-134) may be provided on a card. Such buttons may allow a user to manually provide information to a card. For example, a user may be provided with a personal identification code (e.g., a PIN) and such a personal identification code may be required to be manually inputted into a card using the buttons in order for the card to operate in a particular manner. For example, the use of a magnetic emulator or the use of a display may require a personal identification code.

By dynamically changing a portion of a user's credit card number, for example, credit card fraud is minimized. By allowing the dynamic information to displayed visually to a user, and changed magnetically on a card, user behavior change is minimized (with respect to a credit card with completely static information). By requiring the use of a personal identification code, the fraud associated with lost or stolen credit cards is minimized. Fraud associated with theft/loss is minimized as third party users do not know the personal identification code needed to operate particular aspects of a credit card with dynamic information.

Figure 2:
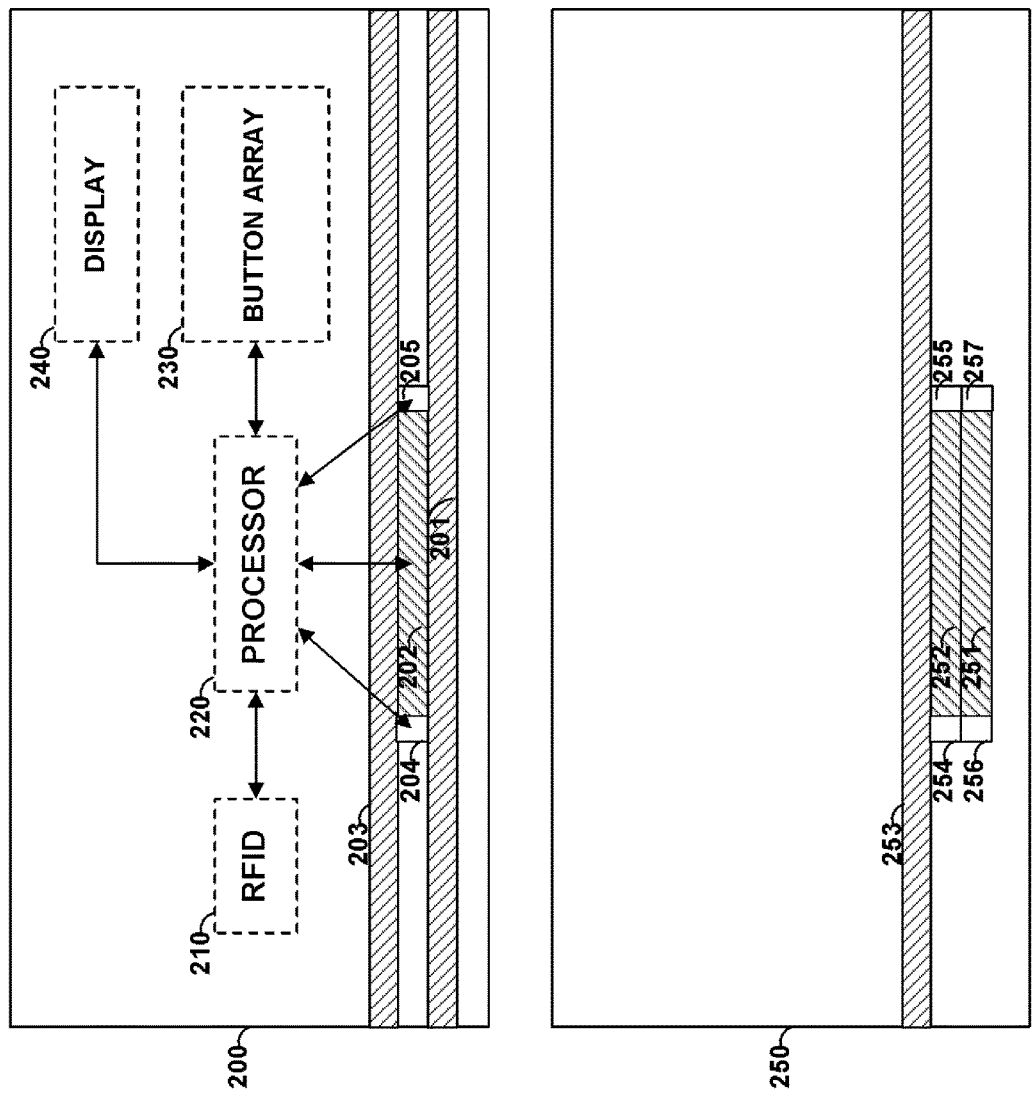
FIG. 2 is an illustration of cards constructed in accordance with the principles of the present invention.
Figure 4:
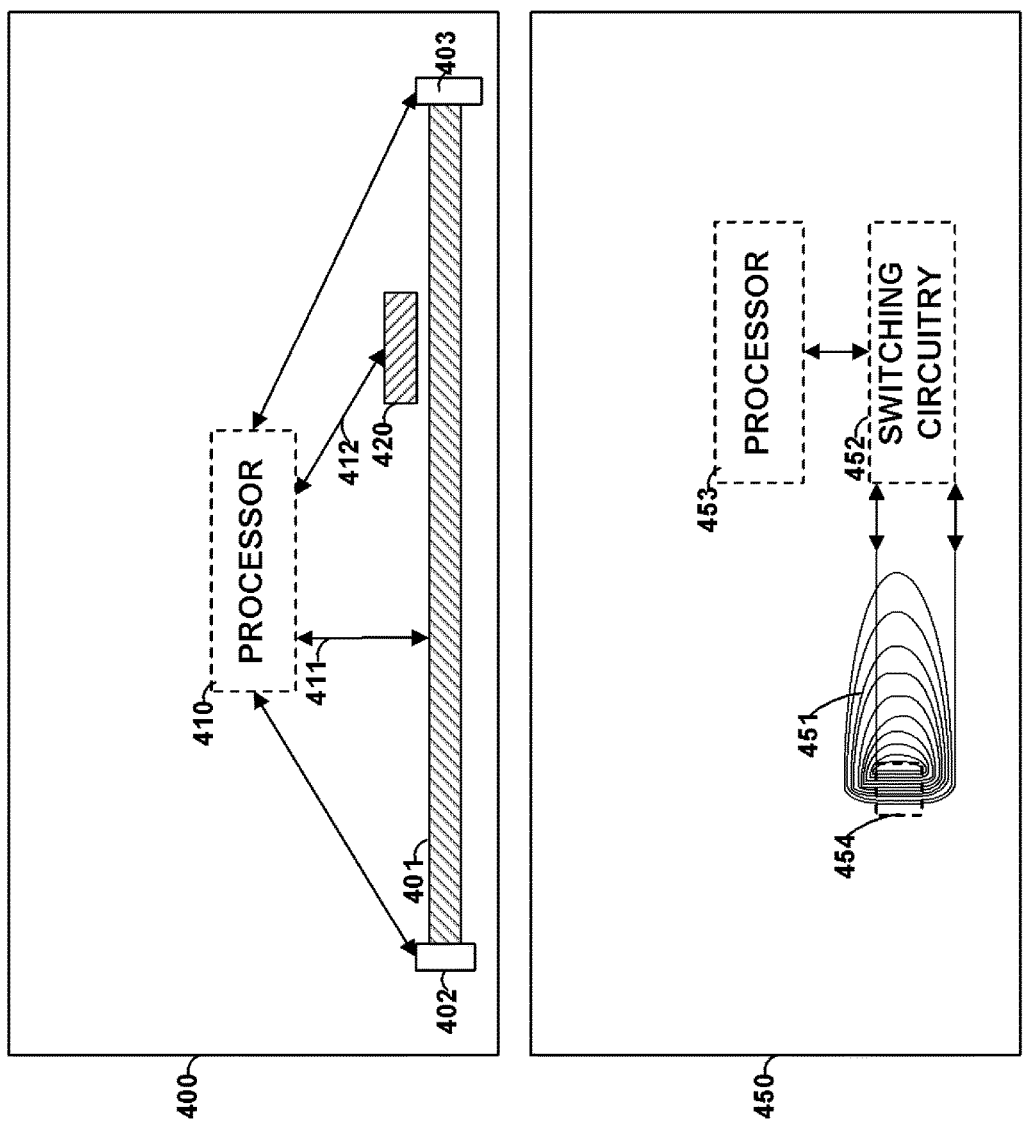
FIG. 4 is an illustration of cards constructed in accordance with the principles of the present invention.

FIG. 2 shows card 200. Card 200 may include, for example, static magnetic stripe track 203, static magnetic stripe track 201, and magnetic emulator 202 sandwiched between read-head detectors 204 and 205. A read-head detector may, for example, be provided as a circuit that detects, for example, changes in capacitance or mechanical coupling to a conductive material. Processor 220 may be provided to, for example, receive information from read-head detectors 204 and 205 and control emulator 202. Persons skilled in the art will appreciate that processor 220 may cause a current to flow through a coil of emulator 202 in a different direction to produce different electromagnetic fields. The transitions between the different electromagnetic fields may be sensed by a magnetic stripe reader as information. Accordingly, a magnetic emulator may transmit data serially while a read-head is electrically coupled with a magnetic reader.

RFID antenna 210 may be provided on card 200. Such an RFID antenna may be operable to transmit information provided by processor 220. In doing so, for example, processor 220 may communicate with an RFID device using RFID antenna 210 and may communicate with a magnetic stripe reader using magnetic emulator 204. Both RFID antenna 210 and magnetic emulator 204 may be utilized to communicate payment card information (e.g., credit card information) to a reader. Processor 240 may also be coupled to display 240 such that dynamic information can be displayed on display 240. Button array 230 may also be coupled to processor 220 such that the operation of card 200 may be controlled, at least in part, by manual input received by button array 230.

Card 250 may be provided and may include static magnetic track 253, magnetic emulators 251 and 252, and magnetic read-heads 254-257). Persons skilled in the art will appreciate that static magnetic track 253 may be a read-write track such that information may be written to magnetic track 253 from a magnetic stripe reader that includes a head operable to magnetically encode data onto a magnetic track. Information may be written to magnetic track 253 as part of a payment process (e.g., a credit card or debit card transaction). Persons skilled in the art will appreciate that a static magnetic track may include a magnetic material that includes ferromagnetic materials that provide for flux-reversals such that a magnetic stripe reader can read the flux-reversals from the static magnetic track. Persons skilled in the art will also appreciate that a magnetic emulator may communicate information that remains the same from payment card transaction to payment card transaction (e.g., static information) as well as information that changes between transactions (e.g., dynamic information).

FIG. 3 shows card 300 that may include magnetic encoders 302 and 302 without, for example, a static magnetic track. Read-head detectors 304-307 may also be provided. Persons skilled in the art will appreciate that a magnetic reader may include the ability to read two tracks of information (e.g., may include at least two read-heads). All of the information needed to perform a financial transaction (e.g., a credit/debit card transaction) may be included on two magnetic tracks. Alternatively, all of the information needed to perform a financial transaction (e.g., a gift card transaction) may be included on one magnetic track. Accordingly, particular cards, or other devices, may include the ability, for example, to only transmit data associated with the tracks that are needed to complete a particular financial transaction. Persons skilled in the art will appreciate that for systems with three tracks of information, the bottom two tracks may be utilized for credit card information. Persons skilled in the art will also appreciate that a secure credit card transaction may be provided by only changing, for example, one of two magnetic tracks utilized in a credit card transaction (for those transactions that utilize two tracks). Accordingly, one track may be a static magnetic track constructed from a magnetic material and the other track may be provided as a magnetic emulator. Persons skilled in the art will also appreciate that numerous additional fields of data may be provided on a magnetic track in addition to a credit card number (or a security code). Dynamic information may be provided in such additional fields in order to complete a particular financial transaction. For example, such additional dynamic information may be numbers (or characters), encrypted with time and synced to software, at a validating server, operable to validate the encrypted number for a particular period of time.

Card 350 includes processor 360. RFID field detector 353 may provide information to processor 350. Additionally, magnetic stripe detectors may provide information to processor 350. An RFID receiver may produce an electromagnetic field that an RFID antenna is operable to electrically couple with and communicate information to. An RFID receiver may act as a source of electrical power to an RFID antenna. Such a power may be harvested (e.g., via RFID 210 of FIG. 2) to charge a rechargeable battery of a card or other device. An RFID field detector may thus be provided to detect an RFID field.

Emulator 351 may be able to generate electromagnetic fields of different frequencies and magnitudes, and operate in different manners, depending on drive signals provided by processor 360. Accordingly, emulator 351 may be driven to electrically couple with an RFID receiver and emulator 351 may also be driven to electrically couple with a magnetic stripe reader. Accordingly, processor 360 may drive emulator 351 to communicate information (e.g., payment information that includes dynamic information) to an RFID receiver when an RFID field is present and to a magnetic stripe reader when a magnetic stripe is present. Accordingly, for example, a multi-purpose emulator is provided. In instances where, for example, both an RFID field and a magnetic stripe reader is detected, processor 360 may select a default communications methodology (e.g., an RFID or magnetic stripe methodology). Processor 360 may be operable to communicate at least two different drive signals to emulator 351 (e.g., signals 391 and 392).

Card 400 shows card 400 that may include processor 400, emulator 401, read-heads 402 and 403, and magnetic stripe encoding receiver 420. Magnetic stripe encoding receiver 420 may be a coil such that a current is induced in the coil when a magnetic stripe encoder attempts to provide a signal that would encode a static magnetic track. Accordingly, receiver 420 may receive information via an encoder such that bi-directional communication can be established with a magnetic stripe reader that includes an encoding capability. Persons skilled in the art will appreciate that a magnetic emulator may be provided that can both transmit data to a read-head of a magnetic stripe reader as well as receive data from an encoding-head of a magnetic stripe reader.

Card 450 includes emulator 451 that includes active region 454 operable to communicate data serially to a magnetic stripe reader. Similarly, for example, emulator 451 may receive information for a magnetic stripe encoder. Persons skilled in the art will appreciate that emulator 451 includes a tail that is spread-out. Such a tail may include the return lines of emulator 451 and may be spaced such that a magnetic reader is not able to pick up the electromagnetic fields generated by such a tail. Accordingly, active region 454 may be spaced close together such that a magnetic stripe reader is able to pick up the cumulative electromagnetic field generated by such an active region. Processor 453 may drive emulator 451 via switching circuitry 452. Switching circuitry 452 may include, for example, one or more transistors that may be utilized to control the direction of current via emulator 451 (e.g., the polarity of voltage(s) across a drive resistor).

Figure 5:
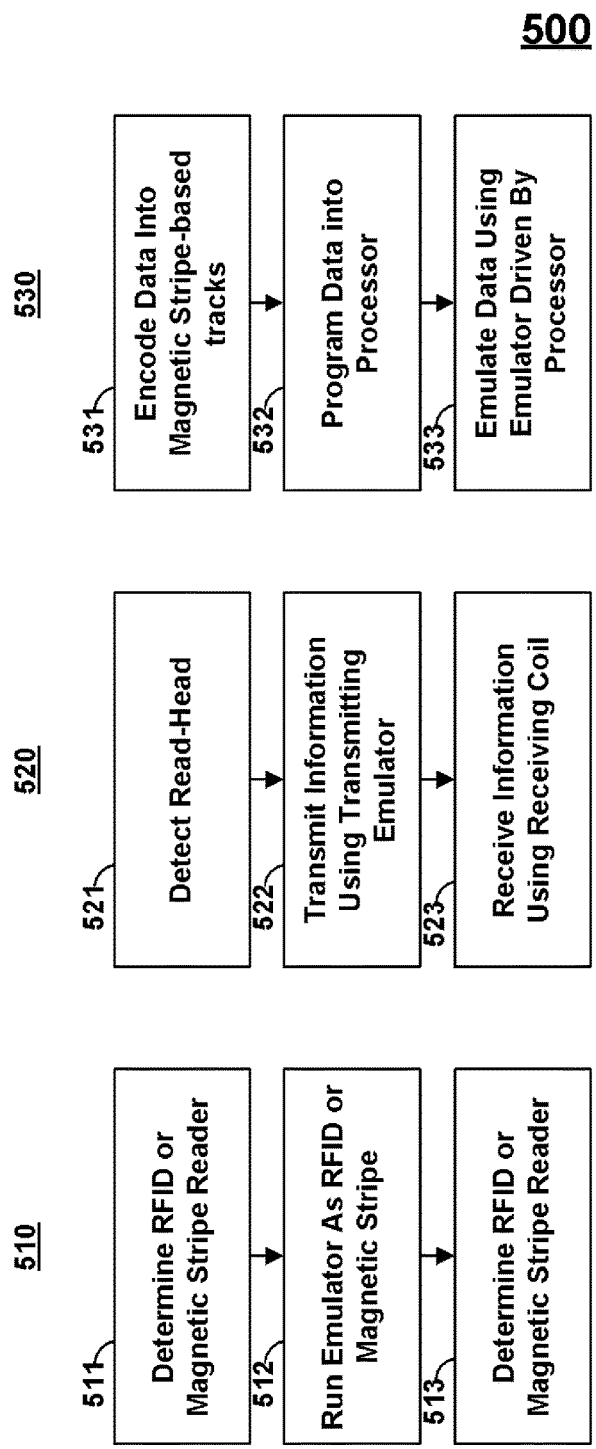
FIG. 5 is an illustration of process flow charts constructed in accordance with the principles of the present invention.

FIG. 5 shows flow chart 510 that may includes steps 511-513. Step 511 may be utilized to determine, of example, whether an RFID or a magnetic stripe reader is within the proximity of a card (or other device). Step 512 may be utilized to run an emulator as an RFID or magnetic stripe in response to step 511. Step 513 may be utilized to determine an RFID and magnetic stripe reader such that the process may be repeated.

Process 520 may be included and may include step 521 to detect a read-head. Step 522 may be included to transmit information using an emulator in a transmitting mode. Step 523 may be utilized to receive information from an emulator (or receiving coil) in a receiving mode. Persons skilled in the art will appreciate that an emulator may be operating in a receiving mode and a transmitting mode at the same time.

Process 530 may be included and may include step 531 to encode data into static magnetic tracks fabricated from a magnetic material. Step 532 may be provided to program data into a processor to be utilized in a subsequent step (e.g., step 533). Step 533 may be utilized to emulate data using an emulator driven by the data programmed in the processor.

Figure 6:
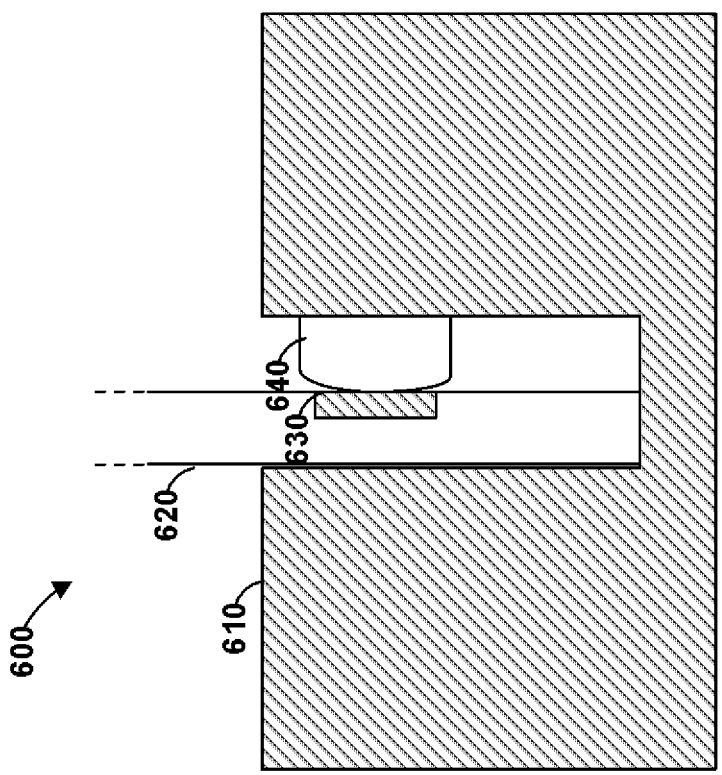
FIG. 6 is an illustration of the electrical coupling between a card and a reader constructed in accordance with the principles of the present invention.

FIG. 6 shows environment 600 that may include magnetic stripe reader 610, read-head housing 640, card 620, and magnetic emulator 630. Read-head housing 640 may include any number of read-head's such as, for example, one, two, or three read-heads. Each read-head may independently receive magnetic fields from magnetic emulator 630 (or a magnetic stripe, such as a magnetic stripe encoded on-card by card 620). Emulator 630 may be positioned to be adjacent to any one or more read-heads of read-head housing 640 or may be positioned to communicate information to any one or more read-heads of read-head housing 640. Persons skilled in the art will appreciate that emulators with longer lengths may be located within the proximity of one or more read-heads for a longer duration of time when a card is swiped. In doing so, for example, more information may be transmitted from an emulator to a read-head when a card is being swiped.

Figure 7:
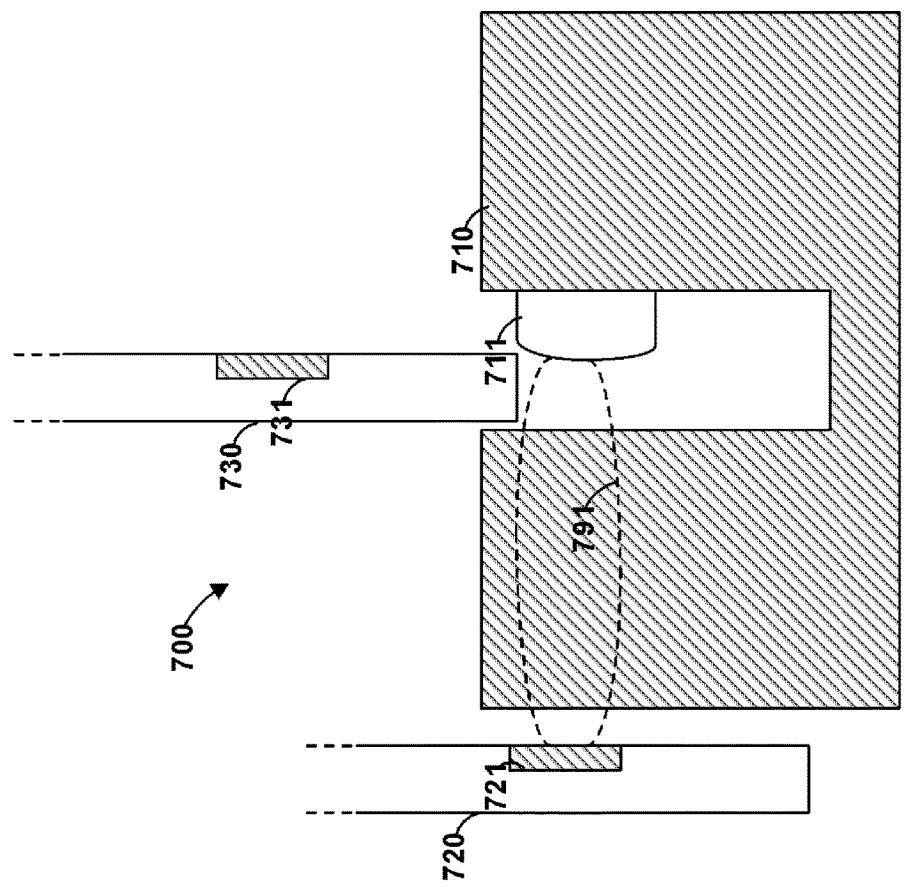
FIG. 7 is an illustration of the electrical coupling between a card and a reader constructed in accordance with the principles of the present invention.
Figure 8:
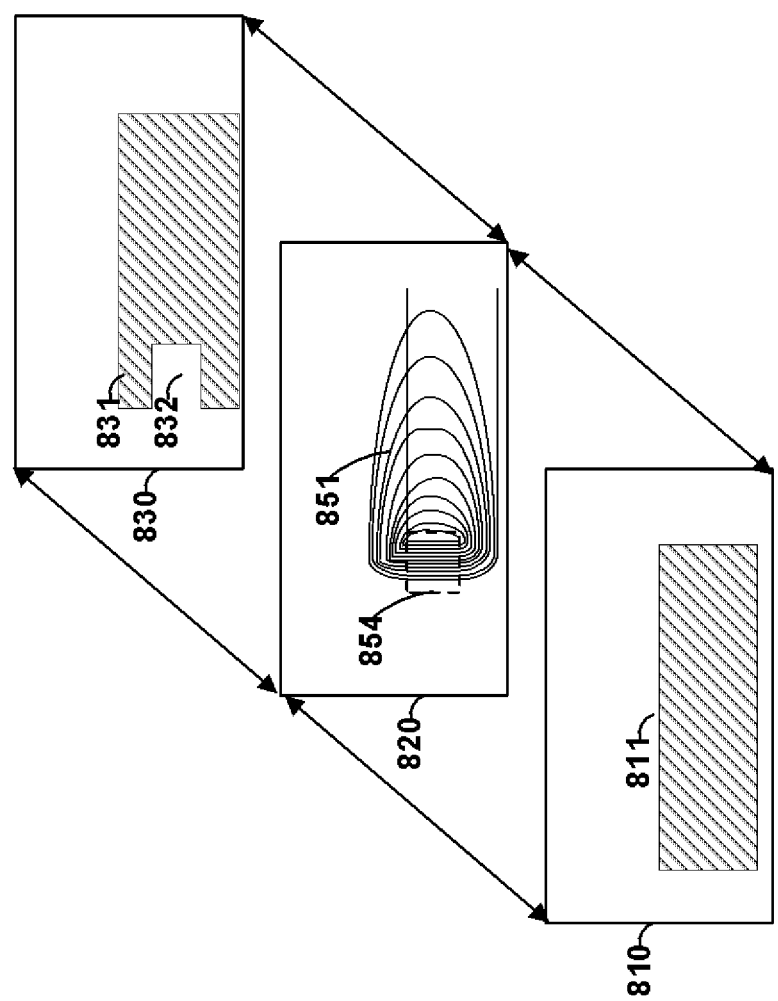
FIG. 8 is an illustration of magnetic shielding in accordance with the principles of the present invention.

FIG. 7 includes environment 700 that may include cards 720 and 730 as well as magnetic stripe reader 710. Read-head housing 711 may be included on a wall of a trough of magnetic stripe reader 710. The trough may be sized to accept cards (e.g., credit cards).

Card 720 may include emulator 721. Emulator 721 may provide electromagnetic field 791 that may transmit through a portion of the housing of magnetic stripe reader 710 (e.g., through a wall of a trough to get to read-head housing 711). Accordingly, card 720 may be located outside of a reader—yet still be operable to communicate information to a magnetic stripe reader. A reader may be provided with an outer wall, for example, with a thickness of a quarter of an inch or more. Emulator 721 can provide electromagnetic field 791 over a distance of, for example, a quarter of an inch or more.

Persons skilled in the art will appreciate that card 720 may be coupled to a device via a permanent or removable cable. Such a device may provide power to card 720 as well as control information—such as control information for emulator 730. An external source of power may be utilized, for example, to provide a larger amount of electrical energy to emulator 721 than from a source of power located within card 720. Persons skilled in the art will appreciate that a car having an internal battery may still be able to receive a cable from a device having its own source of electrical energy.

Card 730 may be provided with emulator 731 and may electrically couple with a read-head of magnetic stripe reader 710. Any number of emulators may be provided in card 730 in any number of orientations such that the appropriate electromagnetic field may couple with a read head of read-head housing 711 regardless of the orientation of card 720 with respect to read-head 711. More particularly, for example, additional read-head housings may be provided in magnetic stripe reader 710 at different locations about the reader to electrically couple with a emulators in a number of different configurations. A sticker and/or guide-structures may be provided on a magnetic stripe reader to, for example, direct a user on how to position his/her card (or other device) for contactless transmission of data (e.g., credit card data) to a read-head housing without using the trough that includes that read-head housing.

Persons skilled in the art will appreciate that a magnetic stripe reader may include a trough that includes two (or more) read-head housings 711 located in approximately the same vertical position on a card-swiping trough, but at different horizontal locations on opposite walls of the trough. In doing so, for example, a magnetic stripe may be read regardless of the direction that a card having the magnetic stripe is facing when the card is swiped. Magnetic emulator 721 may, for example, communicate magnetic fields outside both the front and read surfaces of a card. Accordingly, a single emulator 721 may, for example, couple with a single read-head regardless of the direction the card was facing when swiped. In doing so, for example, the costs of readers may be reduced as only a single read-head may be need to receive information regardless of the direction a card is facing when swiped. Accordingly, magnetic readers do not need stickers and/or indicia to show a user the correct orientation to swipe a card through a magnetic stripe reader. An adapter may be provided that coupled directly to a read-head that allows a device not operable to fit in a trough to electrically couple with a read-head.

An dynamic magnetic communications device, such as a emulator, may be positioned about a surface of a card (or other device), beneath a surface of a device, or centered within a card. The orientation of a magnetic emulator in a card may provide different magnetic fields (e.g., different strength's of magnetic fields) outside different surfaces of a card. Persons skilled in the art will appreciate that a magnetic emulator may be printed via PCB printing. A card may include multiple flexible PCB layers (e.g., FR4 layers) and may be laminated to form a card. Portions of an electronic ink display may also be fabricated on a layer during a PCB printing process.

Magnetic shielding may be provided to limit an electromagnetic field of an emulator. For example, layer 810 may include magnetic shielding 811 (which may be a magnetic material). Magnetic shielding may block magnetic fields from emulator 851 on layer 820. Accordingly, for example, a card may not interact with read-heads blocked from emulator 851 from magnetic shielding 811. In doing so, for example, a magnetic stripe reader may receive information from a single read-head housing at any given time. Layer 830 may be provided, for example, with magnetic shielding 831 that includes an active-region space 832. Accordingly, layer 830 may block magnetic fields from emulator 851 except for those fields generated by active portion 854 (e.g., if space 832 is aligned with active potion 854).

Figure 9:
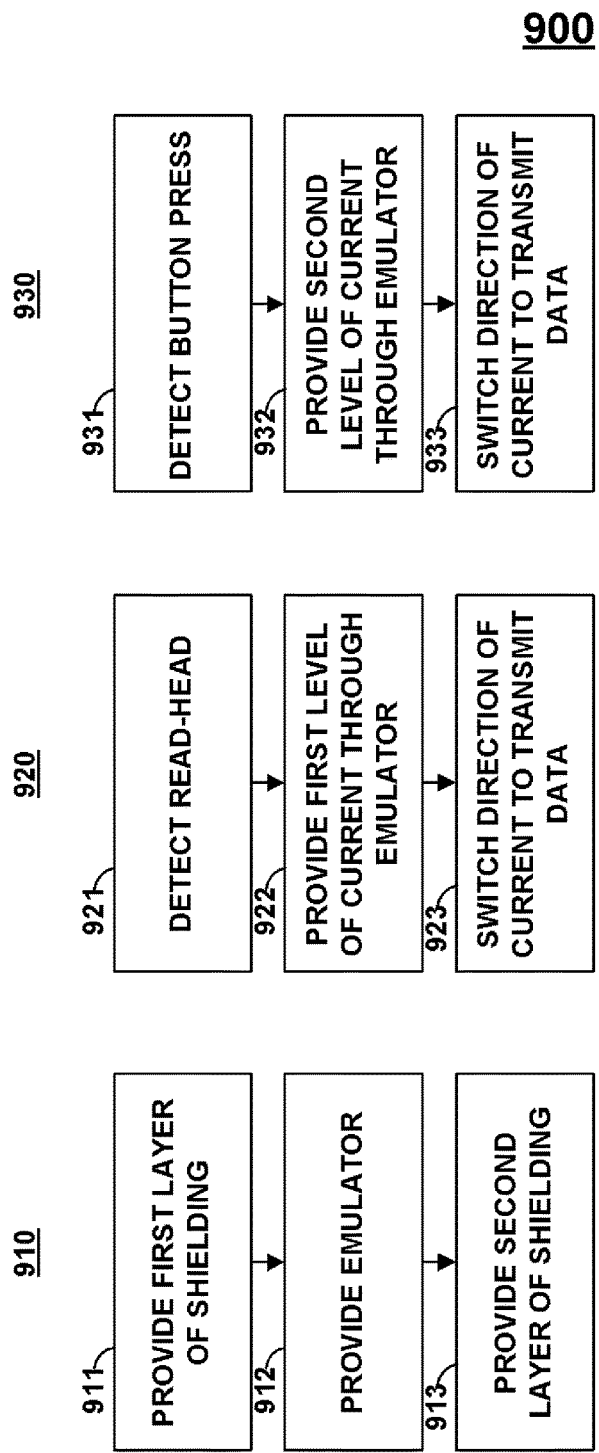
FIG. 9 is an illustration of process flow charts constructed in accordance with the principles of the present invention.

FIG. 9 shows processes 900 that may include flow chart 910. Flow chart 910 may include step 911, in which a first layer of magnetic shielding may be provided (e.g., printed). Step 912 may be provided such that, for example, an emulator is provided (e.g., printed). Step 913 may be included such that, for example, a second layer of shielding may be provided (e.g., printed).

Flow chart 920 may be included. Step 921 may be included in flow chart 920. A read-head may be detected in step 921, a first level of current may be provided through an emulator in step 922, and the direction of the current through the emulator may be switched in step 923 in order to transmit data.

Flow chart 930 may be included. Step 931 may be included in flow chart 930. A button press may be detected in step 931, a second level of current may be provided through an emulator in step 932, and the direction of the current through the emulator may be switched in step 933 in order to transmit data. Flow chart 921 and 931 may be utilized together, for example, to provide a multi-function emulator. For example, an emulator may provide a magnetic-stripe signal to a magnetic stripe reader in flow chart 920 and may provide an RFID signal to an RFID receiver in flow chart 930.

Persons skilled in the art will appreciate that a number does not need to, for example, change with time. Information can change, for example, based on manual input (e.g., a button press or combination of button presses). Additionally, a credit card number may be a static display number and may be wholly or partially displayed by a display. Such a static credit card number may result in the reduction of fraud if, for example, a personal identification code is required to be entered on a manual input entry system to activate the display. Additionally, fraud associated with card cloning may be minimized with the use of a magnetic emulator activated by the correct entry on a manual input entry system.

Person skilled in the art will also appreciate that a card may be cloned by a thief, for example, when the thief puts a illegitimate credit card reader before a legitimate credit card reader and disguising the illegitimate credit card reader. Thus, a read-head detector may detect a read-head housing and then, if a second read-head housing is detected on the same side of the credit card, the reader may transmit information to the second read-head that signifies that two read-head housings were detected. In doing so, for example, a bank, or the police, may be notified of the possibility of the presence of a disguised cloning device. The information representative of multiple read-heads may be included with information that would allow a credit card number to be validated. As such, a server may keep track of the number of read-head housings at each reader and, if more read-head housings are detected than expected, the server may contact an administrator (or the police). The server may also cause the credit card transaction to process or may reject the credit card transaction. If the number of read-head housings (or read-heads) is the number expected by the server, the server can validate the payment transaction.

A payment system using dynamic numbers may, for example, be operable with numbers that are stored outside of the period in which those numbers would otherwise be valid. A server may be included, for example, that accepts a dynamic credit card number, information representative of a past credit card number, and the merchant that is requesting payment. The server may register that merchant for that saved number. The number may be decrypted (or otherwise validated) for that past period of time. Accordingly, the credit card transaction may be validated. Additionally, the merchant identification information may be linked to the stored dynamic credit card number for that past period of time. If the server receives a transaction from a different merchant with that same dynamic credit card number for that same period of time, the server may reject the transaction. In doing so, a merchant may be protected from having credit card numbers stolen from its various storage devices. If a thief steals a number from a merchant's server that is associated with a past period of time, that number cannot be used, for example, anywhere else. Furthermore, such a topology may, for example, allow merchants to provide a one-click shopping, periodic billing, or any other type of feature that may utilize dynamic numbers that are stored and used outside of the period in which the dynamic numbers were generated.

Persons skilled in the art will appreciate that different emulators may be controlled by different switching circuitry (e.g., different transistors). Opto-isolators may be included to protect the processor from any voltage swings driving a magnetic emulator.

Persons skilled in the art will appreciate that multiple buttons may be coupled together to form a single-bit bus. If any button is pressed, the bus may change states and signal to the processor to utilize different ports to determine what button was pressed. In this manner, buttons may be coupled to non-triggerable ports of a processor. Each button (or a subset of buttons) may be coupled to one or more triggerable ports of a processor. A port on a microprocessor may be utilized to drive an emulator in addition to, for example, receiving information from a button. For example, once an appropriate personal identification code is received by a processor, the processor may utilize one or more ports that receive information from one or more buttons to drive an emulator (e.g., for a period of time). Alternatively, for example, a magnetic emulator may be coupled to its own triggerable or non-triggerable processor port. A card may also include a voltage regulator to, for example, regulate power received from an internal or external source of power.

Persons skilled in the art will appreciate that any type of device may be utilized to provide dynamic magnetic information on a card to a magnetic stripe reader. As discussed above, a magnetic encoder may be provided that can change information on a magnetic medium where the changed information can be detected by a magnetic stripe reader.

Figure 10:
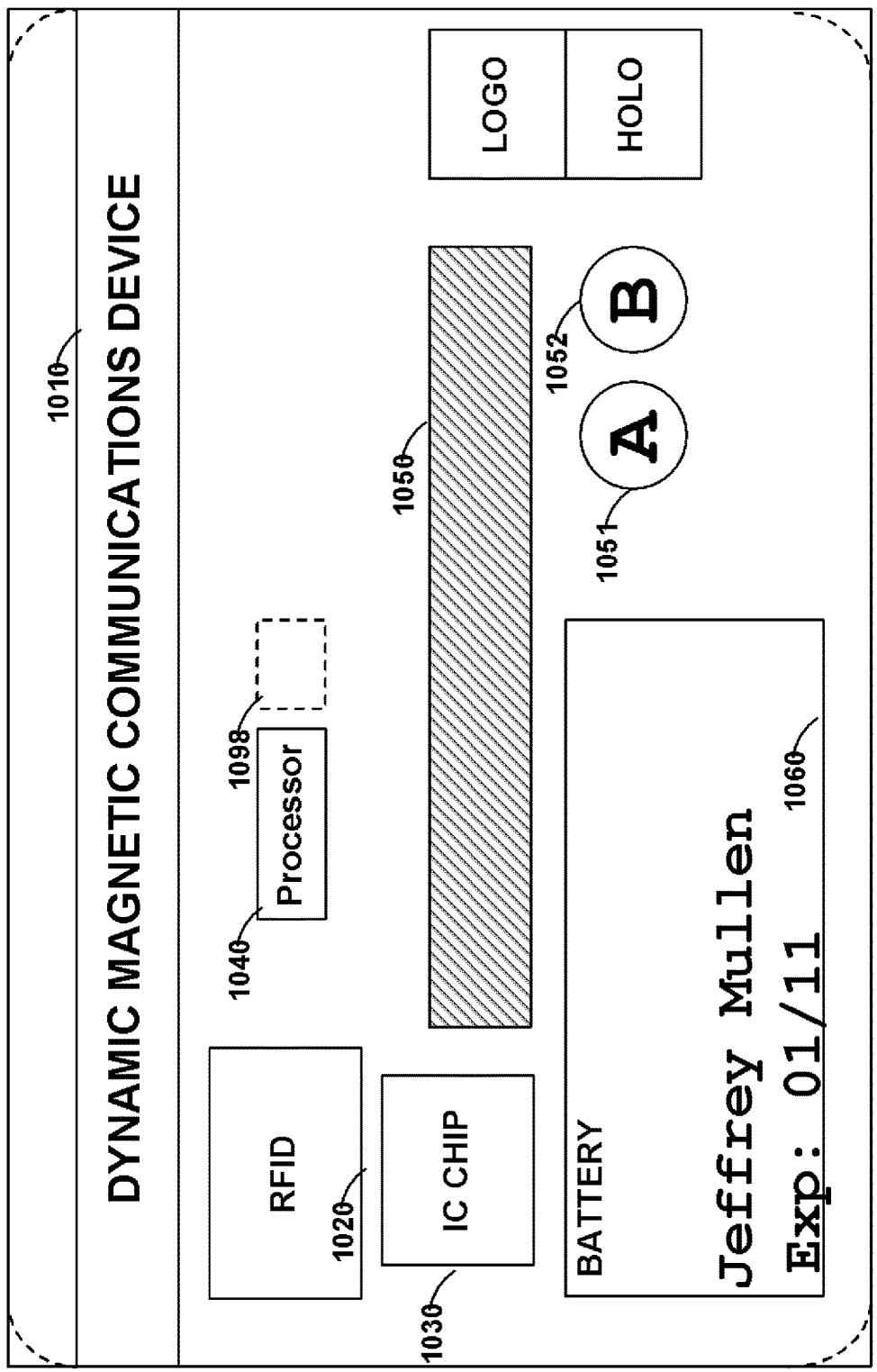
FIG. 10 is an illustration of a card constructed in accordance with the principles of the present invention.

FIG. 10 shows card 1000 that may include, for example, one or more IC chips 1030 (e.g., EMV chips), RFID antennas 1020, processors 1040, displays 1050, dynamic magnetic communications devices 1010 (e.g., magnetic encoders and/or magnetic emulators), batteries 1060, and buttons 1051 and 1052. Additional circuitry 1098 may be provided which may be, for example, one or more oscillators or emulator driving circuits. Persons skilled in the art will appreciate that button 1051 may, for example, be utilized by a user to select one encryption algorithm for a number displayed on display 1050 while button 1052 may be utilized by a user to select a different encryption algorithm. Persons skilled in the art will appreciate that the components of card 1000 may be provided on either surface of a card (e.g., a front or rear surface of the card) or inside of a card. A logo (e.g., of a card issuer) and logo may be provided on either surface of a card.

A button, such as button 1051, may be utilized, for example, to display a number. Such a number may be, for example, encrypted from a secure number based on time or use. For example, one-time use numbers (e.g., a payment number or code) may be retrieved from a list of numbers on memory each time button 1051 is pressed and displayed on display 1050. A processor may only go through each number once on a list. A registration process may be provided in which a user may be requested to enter in a sequence of numbers such that a remote server may validate the card and learn where in a sequence of a list a card currently resides. Numbers may be repeated on a list or may only occur once on a list. All of the numbers available by the length of the number may be utilized by the list or only a portion of the numbers available by the length of the number may be provided by the list. A secret number may be encrypted on a card and a verification server may also have knowledge of this secret number. Accordingly, the remote server may perform the same encryption function as the card on the secret number and verify that the resultant encrypted number is the same as the resultant encrypted number on a card. Alternatively, for example, the remote server may decrypt the received encrypted number to determine the authenticity of the encrypted number and validate an activity (e.g., validate a security access request or a purchase transaction).

Persons skilled in the art will appreciate, for example, that a card may include an IC chip (e.g., EMV chip), RFID, and a dynamic magnetic communications device (e.g., a magnetic emulator or encoder). The same information may be communicated through, for example, any number of such devices (e.g., a dynamic magnetic communications device, RFID, and an EMV chip). A central processor may cause each device to communicate the information (in the same format or a different format). Each component may have its own processor or driving circuitry. Such individual processors or driving circuitry may be coupled to a central processor. An EMV chip may be utilized, for example, to provide control signals to other devices (e.g., circuitry driving a display as well as a dynamic magnetic communications device). Such an EMV chip may receive signals provided by one or more buttons to determine, for example, that a particular button, or sequence of buttons, was pressed by a user.

Persons skilled in the art will appreciate that a read-head housing may include, for example, multiple read-heads. A read-head detector may, more generally, detect a read-head housing and, in doing so, detect a read-head.

Figure 11:
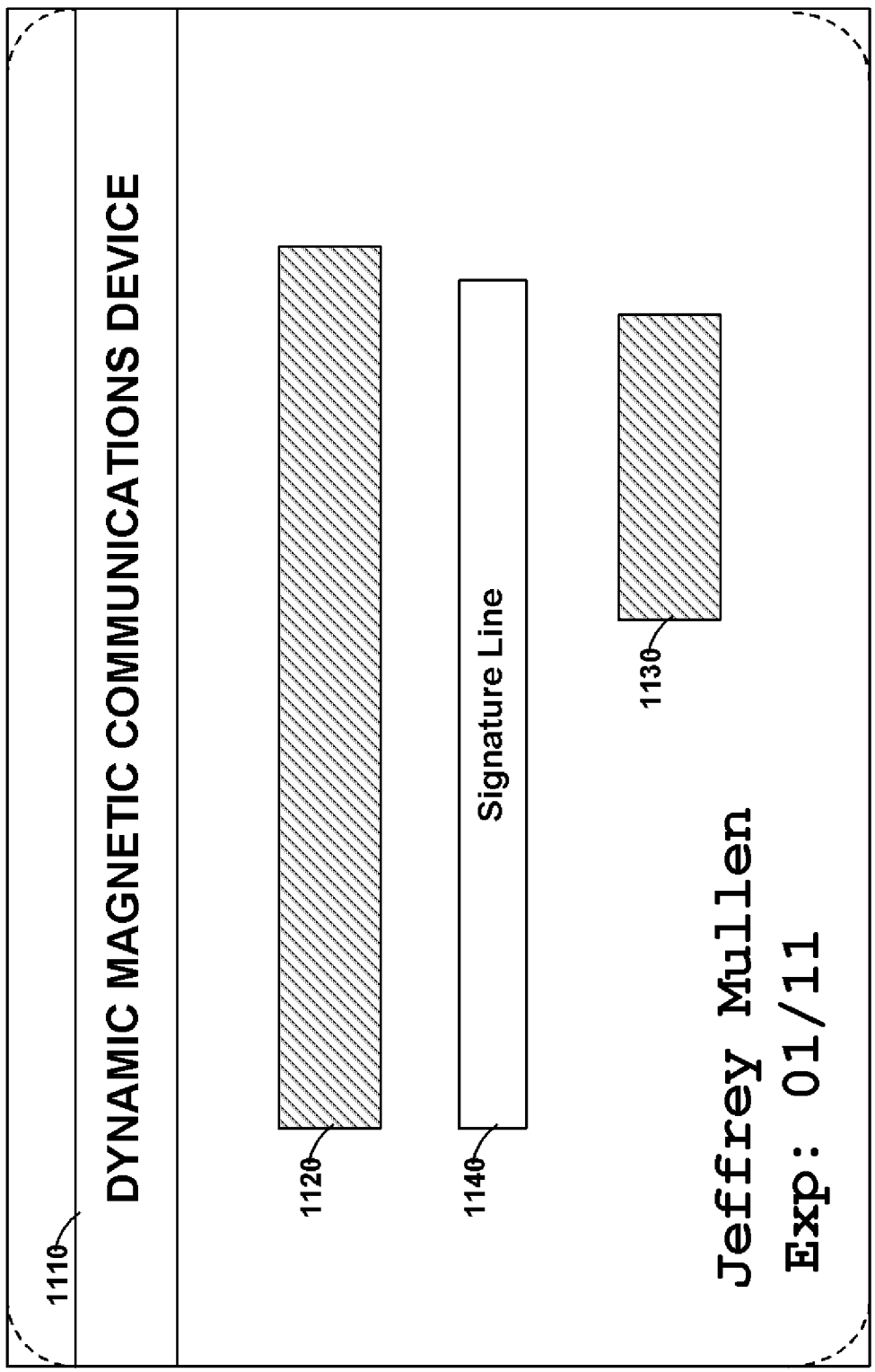
FIG. 11 is an illustration of a card constructed in accordance with the principles of the present invention.

FIG. 11 shows card 1100 that may include, for example, signature area 1140 that may include a material operable to receive marks from a pen (e.g., a signature). Card 1100 may also include, for example, displays 1120 and 1130. Display 1120 may, for example, display a payment number while display 1130 displays a security code (e.g., for online purchase authentication). Display 1120 as well as display 1130 may be utilized on the same side as, for example, dynamic magnetic communications device 1110.

Figure 12:
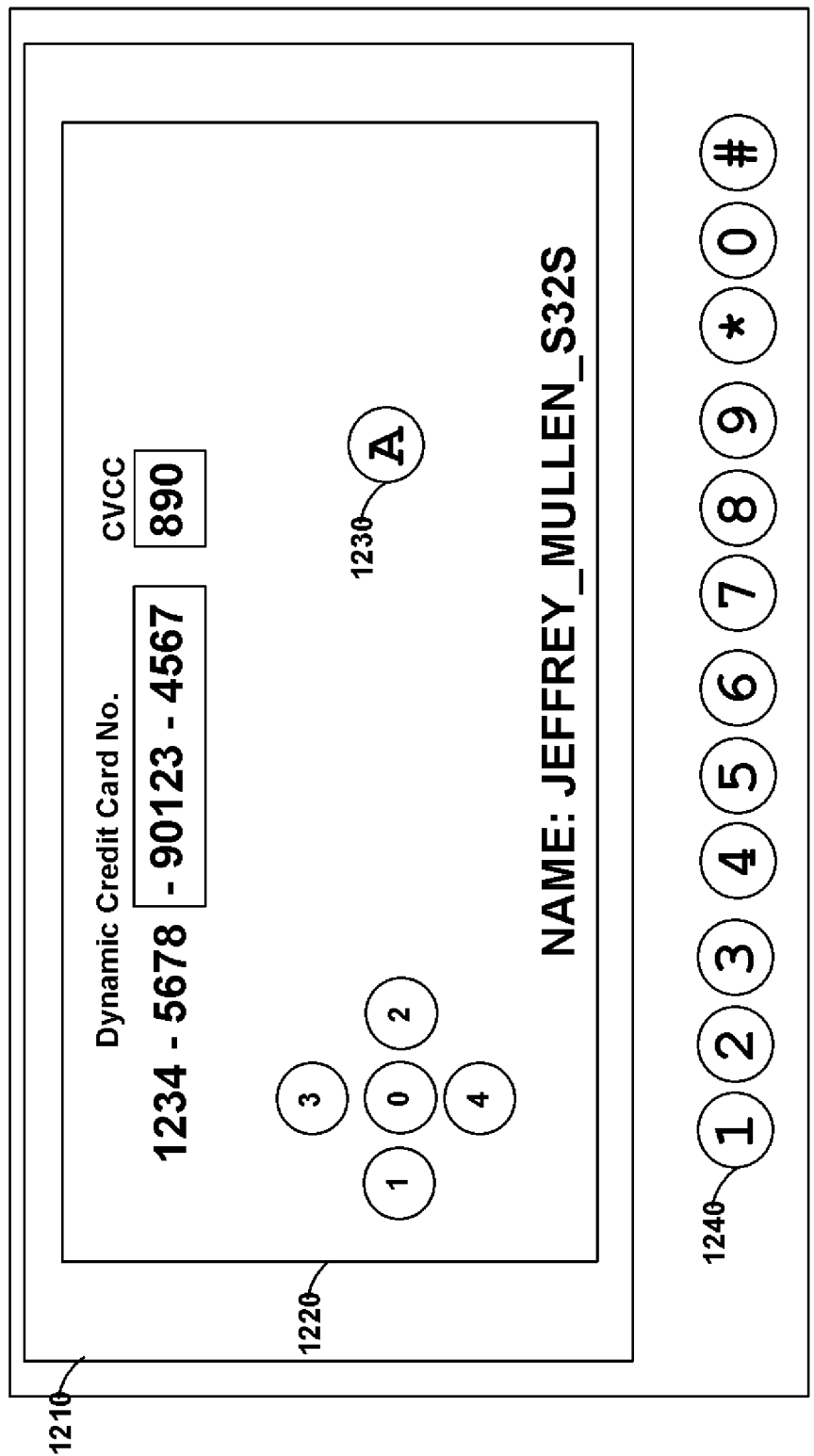
FIG. 12 is an illustration of a personal electronic device constructed in accordance with the principles of the present invention.

FIG. 12 shows personal electronic device 1200 which may be, for example, a portable telephonic device, portable media player, or any type of electronic device. Persons skilled in the art will appreciate that the functionality of a card may be provided on a personal device and displayed through a graphical user interface. Personal electronic device 1200 may include, for example, user inputs 1240 and display 1210. Virtual card 1220 may be displayed on display 1220. Display 1220 may be a touch-sensitive display such that, for example, virtual button 1230 may be provided on virtual card 1220. Persons skilled in the art will appreciate that cards may be provided as virtual cards and a user may interact with such virtual cards in order to provide a variety of functions. Personal electronic device 1200 may communicate to a card reader such as, for example, an RFID reader.

A display may be bi-stable or non bi-stable. A bi-stable display may consume electrical energy to change the information displayed on the bi-stable display but may not consume electrical energy to maintain the display of that information. A non bi-stable display may consume electrical energy to both change and maintain information on the non bi-stable display. A display driving circuit may be provided, for example, for a bi-stable display (or a non bi-stable display). Such a display driving circuit may step-up a supply voltage (e.g., 1-5 volts) to a larger voltage (e.g., 6-15 volts) such that a bi-stable display may change displayed information. A controller (e.g., a processor) may be utilized to control such a display driving circuit. Persons skilled in the art will appreciate that a display may be configured to display numerical data or alphanumerical data. A display may also be configured to display other indicia (e.g., the image of a battery and its remaining life).

A magnetic stripe reader may, for example, determine information on a magnetic stripe by detecting the frequency of changes in magnetic fields (e.g., flux transversals). A particular frequency of flux transversals may correlate to, for example, a particular information state (e.g., a logic "1" or a logic "0"). Accordingly, for example, a magnetic emulator may change the direction of an electromagnetic field at particular frequencies in order to communicate a different state of information (e.g., a logic "1" or a logic "0").

Persons skilled in the art will appreciate that a magnetic emulator may electromagnetically communicate information serially by changing the magnitude of an electromagnetic field with respect to time. As such, for example, a current in a single direction may be provided through a magnetic emulator in order for that magnetic emulator to generate an electromagnetic field of a single direction and a particular magnitude. The current may then be removed from the magnetic emulator such that, for example, the electromagnetic field is removed. The creation of a presence of an electromagnetic field, and the removal of that electromagnetic field, may be utilized to communicate information to, for example, a magnetic stripe reader. A magnetic stripe reader may be configured to read, for example, the change in flux versus time and may associate an increase in an electromagnetic field (e.g., creation of a field) as one flux transversal and a decrease (e.g., removal of a field) as another transversal. In doing so, for example, driving circuitry (not shown) may be provided which, in turn, controls when current is provided to a magnetic emulator. The timing of magnetic flux transversals, as determined by a magnetic stripe reader, may be utilized by that reader to determine whether a logic one ("1") or logic zero ("0") was communicated. Accordingly, a driving circuit may change the frequency of when current is supplied and removed from a magnetic emulator in order to communicate a logic one ("1") or a logic zero ("0").

A driving circuit may, for example, change the direction of current supplied to a magnetic emulator to increase the amount of change in an electromagnetic field magnitude for a period of time. In doing so, for example, a magnetic stripe reader may more easily be able to discern overall changes in an electromagnetic field and, as such, may more easily be able to discern information. As such, for example, a driving circuit may increase the magnitude of an electromagnetic field by providing negative current, decrease the amount of negative current until no current is provided and provide an increasing positive current in order to provide a large swing in the magnitude of an electromagnetic field. Similarly, a driving circuit may switch from providing one amount of negative current (or positive current) to one amount of positive current (or negative current).

Persons skilled in the art will appreciate that a string of a particular bit of data (e.g., a string of logic zeros "0s") may be communicated before as well as after information is communicated through a magnetic emulator. A magnetic stripe reader may utilize such data, for example, to determine base timing information such that the magnetic stripe reader has a timing reference that the reader can utilize to assist in determining timing changes of perceived flux transversals. Accordingly, for example, a magnetic emulator may send data at different overall frequencies and a magnetic stripe reader may be able to reconfigure itself to receive data at such overall frequencies. Information may be encoded using, for example, Frequency/Double Frequency (F2F) encoding such that magnetic stripe readers may perform, F2F decoding.

A processor may control one or more emulators by, for example, controlling the direction of the current supplied through one or more segments of an emulator. By changing the direction of current through a region, for example, the direction of an electromagnetic field may be changed. Similarly, a processor may control one or more emulators by, for example, controlling the change in magnitude of current supplied through one or more segments of an emulator. As such, for example, a processor may increase the magnitude of current as well as decrease the magnitude of current supplied through an emulator. A processor may control the timing of such increases and decreases in current such that a magnetic emulator may, for example, communicate F2F encoded information.

Persons skilled in the art will appreciate that a dynamic magnetic communications device (e.g., a magnetic emulator or magnetic encoder) may be fabricated, either completely or partially, in silicon and provided as a silicon-based chip. Other circuitry (e.g., driving circuitry) may also be fabricated on such a silicon-based chip. A processor, such as a processor for controlling a magnetic communications device, may be, for example, a programmable processor having on-board programmable non-volatile memory (e.g., FLASH memory), volatile memory (e.g., RAM), as well as a cache. Firmware as well as payment information (e.g., dynamic numbers) may be, for example, communicated from a programming device to a processor's on-board programmable non-volatile memory (e.g., a FLASH memory) such that a card may provide a variety of functionalities. Such a processor may also have one or more power-saving operating modes, in which each operating mode turns OFF a different set of circuitry to provide different levels of power consumption. One or more power-savings modes may turn OFF, for example, one or more clocking circuitry provided on a processor. An Application-Specific Integrated Circuit (ASIC) may also be included in a card or other device to provide, for example, processing, dynamic magnetic communications, as well as driving capabilities.

Persons skilled in the art will also appreciate that the present invention is not limited to only the embodiments described. Instead, the present invention more generally involves dynamic information. Persons skilled in the art will also appreciate that the apparatus of the present invention may be implemented in other ways then those described herein. All such modifications are within the scope of the present invention, which is limited only by the claims that follow.

What is claimed is:

1. A device comprising:
    a circuit operable to emit an electromagnetic field and to electrically couple to, and transmit data to, a read-head located on a magnetic stripe reader; and
    a processor for controlling the circuit,
    wherein the circuit is operable to communicate the data to the read-head while located outside of the magnetic stripe reader at a distance of at least a quarter of an inch from the read-head.

2. The device of claim 1, wherein the device is thicker than a payment card.

3. The device of claim 1, wherein the device is a wireless communication device.

4. The device of claim 1, wherein the device is a portable telephonic device.

5. The device of claim 1, wherein the device is a portable media player.

6. The device of claim 1, further comprising a display operable to display a virtual card.

7. The device of claim 1, further comprising a touch-sensitive display operable to display a virtual card.

8. The device of claim 1, wherein the circuit is operable to emit a second electromagnetic field.

9. The device of claim 1, wherein the circuit is operable to emit a second electromagnetic field in parallel with the electromagnetic field.

10. The device of claim 1, wherein the circuit is operable to serially transmit the data.

11. The device of claim 1, wherein the circuit is operable to transmit the data in a parallel operation.

12. A portable telephonic device comprising:
a circuit operable to emit an electromagnetic field and to electrically couple to, and transmit data to, a read-head located on a magnetic stripe reader; and
a processor for controlling the circuit, wherein the circuit is operable to communicate the data to the read-head while located outside of the magnetic stripe reader.

13. The portable telephonic device of claim 12, further comprising a graphical user interface.

14. The portable telephonic device of claim 12, wherein the circuit is operable to communicate the data to the read-head located at a distance of at least a quarter of an inch from the portable telephonic device.

15. The portable telephonic device of claim 12, wherein the portable telephonic device is a portable media player.

16. The portable telephonic device of claim 12, further comprising a display operable to display a virtual card.

17. The portable telephonic device of claim 12, further comprising a touch-sensitive display operable to display a virtual card.

18. The portable telephonic device of claim 12, further comprising a second circuit operable to emit a second electromagnetic field.

19. The portable telephonic device of claim 12, further comprising a second circuit operable to emit a second electromagnetic field in parallel with the electromagnetic field.

20. The portable telephonic device of claim 12, wherein the circuit is operable to serially transmit the data.

* * * * *

(12) INTER PARTES REVIEW CERTIFICATE (2490th)
United States Patent (10) Number: US 10,032,100 K1
Mullen et al. (45) Certificate Issued: Nov. 9, 2021

(54) CARDS AND DEVICES WITH MULTIFUNCTION MAGNETIC EMULATORS AND METHODS FOR USING SAME

(71) Applicants: Jeffrey D. Mullen; David Lambeth; Bruce Cloutier

(72) Inventors: Jeffrey D. Mullen; David Lambeth; Bruce Cloutier

(73) Assignee: DYNAMICS INC.

Trial Number:

IPR2020-00502 filed Jan. 31, 2020

Inter Partes Review Certificate for:

Patent No.: 10,032,100
Issued: Jul. 24, 2018
Appl. No.: 15/137,096
Filed: Apr. 25, 2016

The results of IPR2020-00502 are reflected in this inter partes review certificate under 35 U.S.C. 318(b).

INTER PARTES REVIEW CERTIFICATE
U.S. Patent 10,032,100 K1
Trial No. IPR2020-00502
Certificate Issued Nov. 9, 2021

AS A RESULT OF THE INTER PARTES REVIEW PROCEEDING, IT HAS BEEN DETERMINED THAT:

Claims 1-20 are cancelled.

\* \* \* \* \*